United States Patent
Schillinger et al.

(10) Patent No.: US 9,535,020 B2
(45) Date of Patent: Jan. 3, 2017

(54) ANALYZING AN OBJECT USING A PARTICLE BEAM APPARATUS

(71) Applicant: Carl Zeiss Microscopy GmbH, Jena (DE)

(72) Inventors: Richard Schillinger, Koenigsbronn (DE); Wolfgang Berger, Gerstetten (DE)

(73) Assignee: Carl Zeiss Microscopy GmbH, Jena (DE)

( * ) Notice: Subject to any disclaimer, the term of this patent is extended or adjusted under 35 U.S.C. 154(b) by 0 days.

(21) Appl. No.: 14/972,589

(22) Filed: Dec. 17, 2015

(65) Prior Publication Data

US 2016/0178543 A1   Jun. 23, 2016

(30) Foreign Application Priority Data

Dec. 23, 2014   (DE) .................. 10 2014 226 985

(51) Int. Cl.
   *G01N 23/00*   (2006.01)
   *G01N 23/225*  (2006.01)
   *G01N 23/203*  (2006.01)

(52) U.S. Cl.
   CPC .......... *G01N 23/225* (2013.01); *G01N 23/203* (2013.01); *G01N 23/2252* (2013.01); *G01N 23/2254* (2013.01)

(58) Field of Classification Search
   CPC .......... H01J 37/00; H01J 37/02; H01J 37/244; G01T 1/28

(Continued)

(56) References Cited

U.S. PATENT DOCUMENTS

| 4,897,545 A | 1/1990 | Danilatos |
| 6,087,659 A | 7/2000 | Adler et al. |

(Continued)

FOREIGN PATENT DOCUMENTS

| DE | 101 56 275 A1 | 6/2003 |
| DE | 2009 024 928 A1 | 10/2010 |

(Continued)

OTHER PUBLICATIONS

B. Hornberger et al., "Differential, phase contrast with a segmented detector in a scanning X-ray microprobe", Journal of Synchrotron Radiation, ISSN0909-0495, (2008), 15, 355 and 362.

(Continued)

*Primary Examiner* — Jason McCormack
(74) *Attorney, Agent, or Firm* — Muirhead and Saturnelli, LLC

(57) ABSTRACT

Described herein is a method for analyzing an object using a particle beam apparatus, for example an electron beam apparatus and/or an ion beam apparatus, or using an x-ray beam device and a particle beam apparatus or an x-ray beam device, by means of which the method is carried out. In the method, information about the object is loaded from a data memory into a control device. Furthermore, a group of detection units from the multiplicity of detection units is identified using the information loaded into the control device. A first detector segment is formed from the group of detection units using the control device. Interaction particles and/or interaction radiation, which is/are detected, is/are generated by guiding a particle beam onto the object and scanning the object using the particle beam, where a detector segment signal is read from the detector segment.

16 Claims, 9 Drawing Sheets

(58) Field of Classification Search
USPC .......................................... 250/306, 307, 311
See application file for complete search history.

(56) References Cited

U.S. PATENT DOCUMENTS

| | | |
|---|---|---|
| 6,201,240 B1 | 3/2001 | Dotan et al. |
| 7,525,090 B1* | 4/2009 | Krzeczowski ........ H01J 37/263 250/306 |
| 8,450,820 B2 | 5/2013 | Nanver et al. |
| 8,586,921 B2 | 11/2013 | Boughorbel et al. |
| 8,629,395 B2 | 1/2014 | Morishita et al. |
| 8,729,466 B1 | 5/2014 | Mankos |
| 2003/0116717 A1 | 6/2003 | Knippelmeyer |
| 2008/0033673 A1* | 2/2008 | Anton et al. ............ G01T 1/171 702/70 |
| 2010/0051804 A1* | 3/2010 | Adamec ................ H01J 37/244 250/307 |
| 2012/0037715 A1 | 2/2012 | Sakanoue et al. |
| 2012/0228498 A1 | 9/2012 | Scheid et al. |

FOREIGN PATENT DOCUMENTS

| | | |
|---|---|---|
| DE | 10 2011 012 989 A1 | 9/2012 |
| EP | 2 417 618 B1 | 3/2013 |

OTHER PUBLICATIONS

N. Shibata et al., "Segmented annular all field detector for atomic-resolution scanning transmission electron microscopy", first presented at Gifu (JP), 2012.

A. Mac Raighne et al., "Medipix2 as a highly flexible scanning/imaging detector for transmission electron microscropy", first presented in Cambridge (UK), 2010.

Sol M. Gruner, "Analog X-ray Pixel Detector (APAD) Developments", presented in Grenoble (France), 2005.

T.A. Caswell, et al., "A high-speed area detector for novel imaging techniques in a scanning transmission electron microscope", Ultramicroscopy 109 (2009) 304-311.

B. Hornberger, et al., "Differential phase contrast with a segmented detector in a scanning X-ray microprobe", Journal of Synchrotron Radiation, ISSN0909-0495, (2008), 15, 355-362.

* cited by examiner

ANALYZING AN OBJECT USING A PARTICLE BEAM APPARATUS

TECHNICAL FIELD

This application relates to analyzing an object using a particle beam apparatus, for example an electron beam apparatus and/or an ion beam apparatus, or using an x-ray beam device and more particularly to a particle beam apparatus or an x-ray beam device, by means of which the method is carried out.

BACKGROUND OF THE INVENTION

Electron beam apparatuses, in particular a scanning electron microscope (also referred to as SEM below) and/or a transmission electron microscope (also referred to as TEM below), are used to examine objects (also referred to as samples) in order to obtain knowledge in respect of the properties and behavior of the objects under certain conditions.

In an SEM, an electron beam (also referred to as primary electron beam below) is generated by means of a beam generator and focused on an object to be examined by way of a beam guiding system. The primary electron beam is guided in a gridshaped manner over a surface of the object to be examined by way of a deflection device. Here, the electrons of the primary electron beam interact with the object to be examined. Interaction particles and/or interaction radiation is/are produced as a result of the interaction. By way of example, the interaction particles are electrons. In particular, electrons are emitted by the object—the so-called secondary electrons—and electrons of the primary electron beam are scattered back—the so-called backscattered electrons. The secondary electrons and backscattered electrons are detected by means of at least one particle detector. The particle detector generates detection signals, which are used to generate an image of the object. Thus, an image of the object to be examined is obtained. By way of example, the interaction radiation comprises x-ray radiation and/or cathodoluminescence radiation. The interaction radiation is detected by means of at least one radiation detector, which generates detection signals. By way of example, these detection signals are used to generate spectra, by means of which properties of the object to be examined are determined.

In a TEM, a primary electron beam is likewise generated by means of a beam generator and focused on an object to be examined by means of a beam guiding system. The primary electron beam passes through the object to be examined. When the primary electron beam passes through the object to be examined, the electrons of the primary electron beam interact with the material of the object to be examined. The electrons passing through the object to be examined are imaged onto a luminescent screen or onto a detector—for example in the form of a camera—by a system consisting of an objective. By way of example, the aforementioned system additionally also comprises a projection lens. Here, imaging can also take place in the scanning mode of a TEM. Such a TEM is generally referred to as STEM. Additionally, provision can be made for detecting electrons scattered back at the object to be examined and/or secondary electrons emitted by the object to be examined by means of a further detector in order to image an object to be examined.

The integration of the function of an STEM and an SEM in a single particle beam apparatus is known. It is therefore possible to carry out examinations of objects with an SEM function and/or with an STEM function using this particle beam apparatus.

Furthermore, the prior art has disclosed the practice of analyzing and/or processing an object in a particle beam apparatus using, firstly, electrons and, secondly, ions. By way of example, an electron beam column having the function of an SEM is arranged at the particle beam apparatus. Additionally, an ion beam column is arranged at the particle beam apparatus. Ions used for processing an object are generated by means of an ion beam generator arranged in the ion beam column. By way of example, material of the object is ablated or material is applied onto the object during the processing. The ions are additionally or alternatively used for imaging. The electron beam column with the SEM function serves, in particular, for observing the processing of the object, but it also serves for further examination of the processed or non-processed object.

It is known to detect the interaction particles and/or the interaction radiation with, firstly, a segmented detector and, secondly, a pixel-based detector. This will be explained in more detail below.

The segmented detector has a number of detector segments, wherein each one of the detector segments is respectively connected to an amplifier unit, wherein each amplifier unit in turn is connected to respectively one readout electronics unit. Each individual detector segment has a number of detection units. By way of example, each one of the detection units is respectively embodied as a semiconductor element. As soon as one of the detection units of a detector segment detects interaction particles and/or interaction radiation, a detection signal is generated by this detector segment. Each one of the detector segments generates detection signals. The detection signals of each detector segment are amplified by the amplifier unit associated with the detector segment and subsequently read by the readout electronics unit associated with the detector segment. Known segmented detectors have e.g. up to ten detector segments. This relatively low number of detector segments enables a relatively quick read out of the detection signals from the detector segments.

A known use of a segmented detector lies in the generation of a three-dimensional representation of an object, which is analyzed in a particle beam apparatus. In this known use, images are produced by means of a particle beam using a plurality of detector segments of the segmented detector. The detector segments of the segmented detector are arranged symmetrically about an optical axis of the particle beam apparatus, along which optical axis the particle beam is guided to the object. By way of example, the particle beam is embodied as an electron beam. In particular, the use of a segmented detector with four detector segments is known. Each one of the detector segments generates detection signals, which are respectively used for the image generation. Respectively one image of the object is generated by each one of the detector segments such that a total of four images is generated by means of the known segmented detector. Using the four generated images, gradients along a first axis (e.g. an x-axis) and along a second axis (e.g. a y-axis) are determined for the surface of the object. A grid of profiles, which can be assembled to form a three-dimensional model of the object, is obtained by integrating the gradients along the first axis and the second axis.

As already mentioned above, it is known to detect the interaction particles and/or the interaction radiation using a pixel-based detector. A pixel-based detector is based on the use of semiconductor elements and it is embodied e.g. as a CCD unit or as a CMOS unit. Each pixel is formed by respectively one semiconductor element or respectively one scintillation element. Using such a detector, it is possible, for example, to combine mutually adjacent pixels to form a pixel block. By way of example, a pixel block has m rows and n columns of pixels, with m and n being integers. The pixel block can also be referred to as detector segment. When the semiconductor element or the scintillation element of a pixel detects interaction particles and/or interaction radiation, a detection signal is generated and output as a signal of the pixel block—i.e. as a signal of all the pixels contained in the pixel block.

In the case of the pixel-based detector, it is furthermore possible to subsequently combine groups of pixels to form detector segments after producing an image of the object, as will be explained below. Firstly, an image of the object is recorded using all pixels in the pixel-based detector. After recording the image, groups of pixels are combined to form detector segments visually by means of software or on a monitor. A further image is generated subsequent thereto. The further image is generated by detecting interaction particles and/or interaction radiation by means of the pixel-based detector. The further image is calculated subsequent thereto by means of software, taking into account the determined detector segments, and it is subsequently displayed.

In the known pixel-based detectors, it is disadvantageous that, firstly, the recording speed is low and that, secondly, large amounts of data need to be processed and stored.

In the known segmented detectors, it is disadvantageous that the size and the location of the arrangement of the detector segments at a detection surface of the segmented detector are fixedly prescribed.

In respect to the prior art, reference is made in an exemplary manner to U.S. Pat. No. 8,450,820 B2, US 2013/0037715 A1, U.S. Pat. No. 8,629,395 B2, U.S. Pat. No. 4,897,545, a publication entitled "A high-speed area detector for novel imaging techniques in a scanning transmission electron microscope" by Caswell et al. in Ultramicroscopy 109 (2009) 304-311 and a publication about an x-ray beam device entitled "Differential phase contrast with a segmented detector in a scanning X-ray microprobe" by Hornberger et al in J. Synchrotron Rad. (2008), 15, 355, 362, all of which are incorporated by reference herein.

Accordingly, it is desirable to be able to analyze an object using an analysis apparatus, e.g. a particle beam apparatus or an x-ray beam device, and provide an analysis apparatus for analyzing an object using an analysis apparatus, which, firstly, enables a relatively quick recording of an image of the object and, secondly, enables a high resolution and a good contrast of the image.

SUMMARY OF THE INVENTION

According to the system described herein, an object is analyzed using a particle beam apparatus which comprises at least one beam generator for generating a particle beam with charged particles. Furthermore, the particle beam apparatus is provided with at least one objective lens for focusing the particle beam onto the object. Interaction particles are generated in the case of an interaction between the particle beam and the object. By way of example, the interaction particles are secondary particles and/or scattered particles. In particular, secondary electrons and/or backscattered electrons are generated. In addition or as an alternative thereto, interaction radiation is generated, for example in the form of cathodoluminescence radiation or x-ray radiation.

The particle beam apparatus furthermore has a vacuum region which, for example, is embodied as a sample chamber and/or as a beam guiding tube of the particle beam apparatus. At least one detector for detecting the interaction particles and/or the interaction radiation is arranged in the vacuum region. The detector has at least one detection surface, wherein a multiplicity of detection units are arranged at the detection surface. Each detection unit of the multiplicity of detection units is individually actuatable and individually readable by means of a control device. That is, the control device can access each detection unit of the multiplicity of detection units, read information from each individual detection unit and/or actuate each individual detection unit. By way of example, provision is made in the system described herein for using only a single control device.

Moreover, the particle beam apparatus is provided with at least one data memory, in which information is stored. By way of example, the information comprises information about an interaction behavior of the particle beam with the material of the object and/or information about solid angle regions, in which the interaction particles propagate after the generation thereof and/or into which the interaction radiation is emitted after the generation thereof. In one embodiment of the system described herein, the information is established prior to carrying out the method according to the system described herein using e.g. known reference objects (also referred to as calibration objects) and stored in the data memory. In a further embodiment, the information is established when carrying out the method and stored in the data memory. The interaction behavior of the particle beam with the material of the object and/or the solid angle regions, in which the interaction particles propagate after the generation thereof and/or into which the interaction radiation is emitted after the generation thereof, is/are characteristic for the properties of the object, e.g. the material of the object, a crystal orientation of the object and/or a material structure of the object. In a further exemplary embodiment, the solid angle regions, in which the interaction particles propagate after the generation thereof and/or into which the interaction radiation is emitted after the generation thereof, are dependent on the setting parameters of the particle beam apparatus, for example an acceleration voltage for accelerating the charged particles in the particle beam apparatus and/or a focusing voltage for focusing the particle beam. However, the system described herein is not restricted to these setting parameters. Rather, any suitable setting parameter is utilizable in this embodiment. This exemplary embodiment assumes that it is possible to decisively influence and control the behavior of the interaction particles and/or of the interaction radiation on account of the setting parameters and independently of the nature of the object such that the aforementioned solid angle regions are determinable, e.g. by means of a calculation.

On the basis of this information, it is possible to identify regions on the object which appear of particular interest for a further analysis. This is explained in more detail below.

The particle beam apparatus is furthermore provided with an analysis unit for analyzing the object. By way of example, the analysis unit is embodied as a computer with a screen. In particular, provision is made for evaluating detection signals of the detection units in the analysis unit and, in particular, for using these to generate an image of the object. The system described herein has the following method steps:

In one method step, a group—namely a first group—of detection units is identified from the multiplicity of detection units by means of the information stored in the data memory.

As already mentioned above, the interaction behavior of the particle beam with the material of the object and/or the solid angle regions, in which the interaction particles propagate after the generation thereof and/or into which the interaction radiation is emitted after the generation thereof, is/are characteristic for the properties of the object, for example the properties already mentioned above. On the basis of this information, it is possible to identify regions on the object which appear of particular interest for a further analysis and/or processing. The detection units which, in particular, cover the aforementioned solid angle regions are identified from the multiplicity of detection units and they form the aforementioned first group.

In a further method step, there now is combining of the first group of detection units to form a first detector segment. After the combining, the detection units of the first group form the first detector segment. Expressed in other words, the first detector segment is formed by the first group of detection units. There now is loading of the information about the first detector segment into the control device.

There now is guiding of the particle beam onto the object and scanning of the object using the particle beam. In the process, interaction particles and/or interaction radiation are produced. These are detected by the detector. However, detection signals from the individual detection units are not read out now. Rather, provision is now made in this method step of reading a first detector segment signal from the first detector segment. The first detector segment signal is provided by the first detector segment when at least one detection unit of the first group detects interaction particles and/or interaction radiation. Then, a representation of the object is generated by means of the first detector segment signal. By way of example, the representation is an image of the surface of the object. In a further method step there now is an analysis of the object by means of the representation of the object in the analysis unit and/or using the analysis unit.

The system described herein unifies the advantages of a pixel-based detector with the advantages of a segmented detector. By way of example, it is possible to select the size, form and composition of the detector segments on the basis of predeterminable criteria. The size, form and the composition of the detector segments is not fixedly predetermined in the system described herein. Rather, the size, the form and the composition of the detector segments can be selected in a suitable manner which appears particularly suitable for analyzing a specific region of interest. Furthermore, like the segmented detector from the prior art, the system described herein renders it possible to read detector segment signals relatively quickly and generate a representation, by means of which the object can be analyzed.

The selection of the detector segments, in particular the number thereof, and the detection units associated with a specific detector segment—for example pixel units in the form of semiconductor elements (e.g. photodiodes)—is, in principle, arbitrary and it is brought about, for example, depending on the object to be examined. By way of example, provision is made in one embodiment of assigning mutually adjacent detection units to a single detector segment. In an in turn further embodiment of the system described herein, provision is additionally or alternatively made of assigning to a single detector segment detection units which are spaced apart from one another and which do not adjoin one another locally.

As already mentioned above, the size and form of the individual detector segments is selectable. By way of example, at least one detector segment can have a square, circular ring-shaped, circular, ring segment-shaped or cross-shaped embodiment. However, the system described herein is not restricted to the aforementioned embodiments. Rather, any suitable form is selectable. Furthermore, it is advantageous that the information about the detector segment is loaded into the control device, which e.g. is embodied as part of the detector, and that the control device generates the detector segment from the detector units using the loaded information about the detector segment. This ensures a free selection of the size and form of the individual detector segments and a quite fast readout of the detector segment signals for generating the representation of the object, which is used to analyze the object.

In one embodiment of the method according to the system described herein, provision is additionally or alternatively made for the information to be loaded into the control device from the data memory. The identification of the first group of detection units is then brought about by means of the information loaded into the control device. Furthermore, the formation of the first detector segment from the first group of detection units is brought about using the control device.

In one embodiment of the method according to the system described herein, there also is an identification of a further group—namely a second group—of detection units from the multiplicity of detection units, for example by means of the information loaded into the control device. What is mentioned further above also applies here. The interaction behavior of the particle beam with the material of the object and/or the solid angle regions, in which the interaction particles propagate after the generation thereof and/or into which the interaction radiation is emitted after the generation thereof, is/are characteristic for the properties of the object, which properties were already mentioned above. On the basis of this information, it is possible to identify regions on the object which appear of particular interest for a further analysis and/or processing. The detection units which cover the aforementioned solid angle regions are identified from e.g. the multiplicity of detection units and they form the aforementioned second group. In a further method step, there now is combining of the second group of detection units to form a second detector segment. After the combining, the detection units of the second group form the second detector segment. Expressed in other words, the second detector segment is formed by the second group of detection units. Information about the second detector segment is loaded into the control device. Furthermore, a second detector segment signal is read from the second detector segment. The second detector segment signal is provided by the second detector segment when at least one detection unit of the second group detects interaction particles and/or interaction radiation.

By way of example, two groups of detection units are identified from the multiplicity of detection units in the method according to the system described herein, namely a first group of detection units and a second group of detection units. However, reference is explicitly made to the fact that the system described herein is not restricted to the identification of two groups of detection units. Rather, provision is made in the system described herein for identifying any number of groups which is suitable for carrying out the method according to the system described herein. As mentioned above, the identification of a single group and the formation of a single detector segment suffice for the system described herein. As an alternative thereto, it is possible, for example, to identify up to ten groups or up to twenty groups. Further exemplary embodiments provide for the identification of more groups or fewer groups.

In a further embodiment of the method according to the system described herein, the representation already mentioned above is a first representation. Expressed in other words, the representation, on the basis of which the analysis of the object is carried out in the analysis unit and/or using the analysis unit, is referred to as first representation. In this exemplary embodiment, the information stored in the data memory (e.g. information about the object) is established as follows and subsequently stored in the data memory. The particle beam is initially guided onto the object. To be more precise, the particle beam is focused onto the object by means of the objective lens. The surface of the object is scanned by means of the particle beam. Interaction particles and/or interaction radiation is/are produced as a result of an interaction between the particle beam and the material of the object—as already mentioned above. Said interaction particles and/or interaction radiation is/are detected by the detector, wherein respectively one detection signal is read from each one of the detection units of the multiplicity of detection units by means of the control device. Expressed in other words, the interaction particles and/or the interaction radiation is/are detected using the detector. Each detection unit of the multiplicity of detection units respectively generates one detection signal. Each one of these detection signals is read by means of the control device. The read detection signals are used to generate a second representation of the object. By way of example, the second representation is an image of a surface of the object or an intensity distribution. The second representation is stored in the data memory as information and loaded into the control device while carrying out the method according to the system described herein. By way of example, the first group and/or the second group of detection units are now identified in a further method step from the multiplicity of detection units on the basis of the second representation of the object.

The identification of the groups of detection units can be carried out as desired. However, provision is additionally or alternatively made in one exemplary embodiment of the method according to the system described herein for the identification of the groups of detection units, in particular the first group of detection units and/or the second group of detection units, to be carried out visually. By way of example, certain regions of interest are identified by a user on the basis of the information loaded into the data memory and/or into the control device—for example on the basis of the second representation stored in the data memory. Then, the user selects the groups of detection units e.g. in such a way that the selected detector segments acquire precicely the particular properties of the regions of interest. Expressed using other words, the selected detector segments preferably generate detection signals which are generated from these regions of interest on the basis of the interaction particles and/or interaction radiation. The visually selected group, or the visually selected groups, of detection units, e.g. the first group and/or the second group of detection units, is/are then stored in the control device. Each one of the visually selected groups of detection units can form a detector segment, by means of which the further method according to the system described herein is then carried out.

As already mentioned above, the information stored in the data memory additionally or alternatively comprises an intensity distribution in one embodiment of the system described herein. Therefore, in this embodiment, provision is made for the identification of the first group of detection units from the multiplicity of detection units to be carried out by means of the intensity distribution. Additionally or alternatively, provision is made for the identification of the second group of detection units from the multiplicity of detection units to be likewise carried out by means of the intensity distribution. These embodiments are based on the consideration that regions of the object which have a high intensity in the intensity distribution of the selected detection units could be of interest for a closer examination. This includes e.g. strong intensity regions—in particular intensity maxima—which can be seen in the intensity distribution in the form of diffraction images of objects, e.g. crystalline objects.

In a further exemplary embodiment of the method according to the system described herein, provision is additionally or alternatively made for the detector segment signals, in particular the first detector segment signal and the second detector segment signal, to be read out successively and to be transmitted to the analysis unit by way of a single line. As an alternative thereto, provision is made for transmitting the detector segment signals to the analysis unit by way of different lines. In particular, provision is made for the first detector segment signal to be transmitted to the analysis unit by way of a first line and for the second detector segment signal to be transmitted to the analysis unit by way of a second line.

All exemplary embodiments of the method according to the system described herein are suitable for being carried out in an automated fashion. By way of example, it is possible to identify regions with a high contrast and/or regions with a high intensity by means of image recognition software and accordingly fix these locally. Identifying and combining detection units to form detector segments is then carried out in such a way that the detector segments detect interaction particles and/or interaction radiation from these identified regions in a targeted manner.

The system described herein also relates to a computer program product comprising program code, which can be loaded or is loaded into a processor and which, when executed, controls a particle beam apparatus in such a way that a method having at least one of the features specified above or specified further below or having a combination of at least two of the features specified above or specified further below is carried out.

The system described herein furthermore relates to a particle beam apparatus for analyzing an object, wherein the particle beam apparatus is provided for carrying out the method according to the system described herein. The particle beam apparatus comprises at least one beam generator for generating a particle beam with charged particles. Furthermore, the particle beam apparatus is provided with at least one objective lens for focusing the particle beam onto the object. The particle beam apparatus furthermore comprises a vacuum region. By way of example, the vacuum region is embodied as a sample chamber of the particle beam apparatus and/or e.g. as part of a beam guiding tube of the particle beam apparatus. At least one detector for detecting interaction particles and/or interaction radiation is arranged in the vacuum region. The detector has at least one detection surface, wherein a multiplicity of detection units are arranged at the detection surface. Each detection unit of the multiplicity of detection units generates a detection signal when it detects the interaction particles and/or the interaction radiation. Each detection unit of the multiplicity of detection units is individually actuatable and/or readable by means of a control device. In one embodiment of the particle beam apparatus, provision is made for the particle beam apparatus to have only one single control device for the multiplicity of detection units. Furthermore, the particle beam apparatus according to the system described herein has at least one data memory which is configured to store information during operation or in which information is stored. As already explained further above, this information comprises e.g. information about an interaction behavior of the particle beam with the material of the object and/or information about solid angle regions, in which the interaction particles propagate after the generation thereof and/or into which the interaction radiation is emitted after the generation thereof. In respect of the information, all statements already made above and the statements still noted further down apply.

Additionally, the particle beam apparatus according to the system described herein comprises at least one analysis unit for analyzing the object, and at least one processor, in which an aforementioned computer program product is loaded.

In one exemplary embodiment of the particle beam apparatus according to the system described herein, provision is additionally or alternatively made for the control device to be arranged in the vacuum region of the particle beam apparatus, for example in the sample chamber of the particle beam apparatus. In particular, provision is made for the detector and the control device to form one unit. Expressed in other words, the control device is part of the detector.

In an embodiment of the particle beam apparatus according to the system described herein, provision is additionally or alternatively made for the detector to have a detector head. The detector head is arranged in the vacuum region. The detection surface is arranged on the detector head. The control device is likewise arranged in the detector head. As already mentioned above, provision is made, for example, for loading the information about the detector segments into the control device. Hence, this information is directly transmitted into a part of the detector, wherein this part of the detector is arranged in the vacuum region. Expressed in other words, the information about the detector segments is loaded into the detector and stored in the detector.

In a further embodiment of the particle beam apparatus according to the system described herein, provision is additionally or alternatively made for the beam generator to be a first beam generator and for the particle beam to be embodied as a first particle beam with first charged particles. The objective lens is embodied as a first objective lens for focusing the first particle beam onto the object. The particle beam apparatus furthermore comprises at least a second particle beam generator for generating a second particle beam with second charged particles. Furthermore, the particle beam apparatus is provided with at least one second objective lens for focusing the particle beam onto the object. In an in turn further embodiment of the particle beam apparatus according to the system described herein, provision is additionally or alternatively made for the particle beam apparatus to be an electron beam apparatus and/or an ion beam apparatus.

The system described herein still relates to a further method which is based on the method already described further above. Therefore, all statements made above also apply in respect of the further method now described below. The further method serves to analyze an object using an x-ray beam device, e.g. an x-ray microprobe. The x-ray beam device comprises at least one beam generator for generating x-rays. The x-rays are focused on an object by means of an appropriate focusing device, e.g. a zone plate. Imaging an object is brought about by scanning of the object and detecting the interaction radiation at each scanning point. In the case of e.g. an x-ray microprobe, scanning is brought about by a movement. In particular, provision is made for the scanning to be brought about by way of a movement of the object in relation to the stationary x-ray beam device, e.g. the x-ray microprobe. Alternatively, provision is made for the scanning to be carried out by scanning the focused x-ray beam over the object. Interaction radiation is generated during the interaction between the x-ray beams and the object. In principle, the interaction radiation is that portion of the x-ray beams which can be transmitted through the object and can be detected. For detection purposes, the x-ray beam device comprises at least one detector for detecting the interaction radiation. The detector is provided with at least one detection surface, wherein a multiplicity of detection units are arranged at the detection surface, wherein each detection unit of the multiplicity of detection units is individually actuatable and readable by way of a control device. By way of example, the individual detection units can also be embodied as a scintillation unit in each case. The x-ray beam device moreover comprises at least one data memory, in which information is stored, wherein the information comprises information about an interaction behavior of the x-rays with the material of the object and/or information about solid angle regions, into which the interaction radiation is emitted after the generation thereof. For the purposes of analyzing the object, the x-ray beam device is embodied with at least one analysis unit for analyzing the object.

In the further method, a group—namely a first group—of detection units is identified from the multiplicity of detection units by means of the information stored in the data memory. As already mentioned above, the solid angle regions, into which the interaction radiation is emitted after the generation thereof, are characteristic for the properties of the object, for example for the properties already mentioned further above. On the basis of this information, it is possible to identify regions on the object which appear of particular interest for a further analysis and/or processing. The detection units which, in particular, cover the aforementioned solid angle regions are identified from the multiplicity of detection units and they form the aforementioned first group. In a further method step, there now is combining of the first group of detection units to form a first detector segment. After the combining, the detection units of the first group form the first detector segment. Expressed in other words, the first detector segment is formed by the first group of detection units. There now is loading of the information about the first detector segment into the control device. The x-rays are now guided onto the object. Interaction radiation is produced in the process. It is detected by the detector. However, detection signals from the individual detection units are not read out now. Rather, provision is now made in this method step of reading a first detector segment signal from the first detector segment. The first detector segment signal is provided by the first detector segment when at least one detection unit of the first group detects interaction radiation. Then, a representation of the object is generated by means of the first detector segment signal. In a further method step there now is an analysis of the object by means of the representation of the object in the analysis unit and/or using the analysis unit.

The system described herein also relates to a computer program product comprising program code, which can be loaded or is loaded into a processor and which, when executed, controls an x-ray beam device in such a way that the further method, which has at least one of the features specified above or specified further below or having a combination of at least two of the features specified above or specified further below, is carried out.

In order to carry out the further method, the system described herein furthermore relates to an x-ray beam device for analyzing an object, wherein the x-ray beam device is embodied e.g. as an x-ray microprobe. The x-ray beam device comprises at least one beam generator for generating x-rays, a focusing device, for example in the form of a zone plate, for focusing the x-rays onto the object and at least one detector for detecting interaction radiation, wherein the interaction radiation is generated by an interaction between the x-rays and the object. The detector has at least one detection surface, wherein a multiplicity of detection units are arranged at the detection surface. Each detection unit of the multiplicity of detection units generates a detection signal when it detects the interaction radiation. Each detection unit of the multiplicity of detection units is individually actuatable and/or readable by means of a control device. In one embodiment of the x-ray beam device, provision is made for the x-ray beam device to have only one single control device for the multiplicity of detection units. Furthermore, the x-ray beam device according to the system described herein has at least one data memory which is configured to store information during operation or in which information is stored. As already explained further above, this information comprises e.g. information about an interaction behavior of the x-rays with the material of the object and/or information about solid angle regions, into which the interaction radiation is emitted after the generation thereof. In respect of the information, all statements already made above and the statements still noted further down apply. Additionally, the x-ray beam device according to the system described herein comprises at least one analysis unit for analyzing the object, and at least one processor, in which an aforementioned computer program product in relation to the further method is loaded.

Below, the system described herein is explained in more detail on the basis of exemplary embodiments by means of the figures. In detail:

DETAILED DESCRIPTION OF VARIOUS EMBODIMENTS

The system described herein is now explained in more detail by means of particle beam apparatuses in the form of an SEM and in the form of a combination apparatus, which has an electron beam column and an ion beam column. Reference is explicitly made to the fact that the system described herein can be used in each particle beam apparatus, in particular in each electron beam apparatus and/or in each ion beam apparatus. Moreover, the system described herein can also be used in an x-ray beam apparatus.

Figure 1:
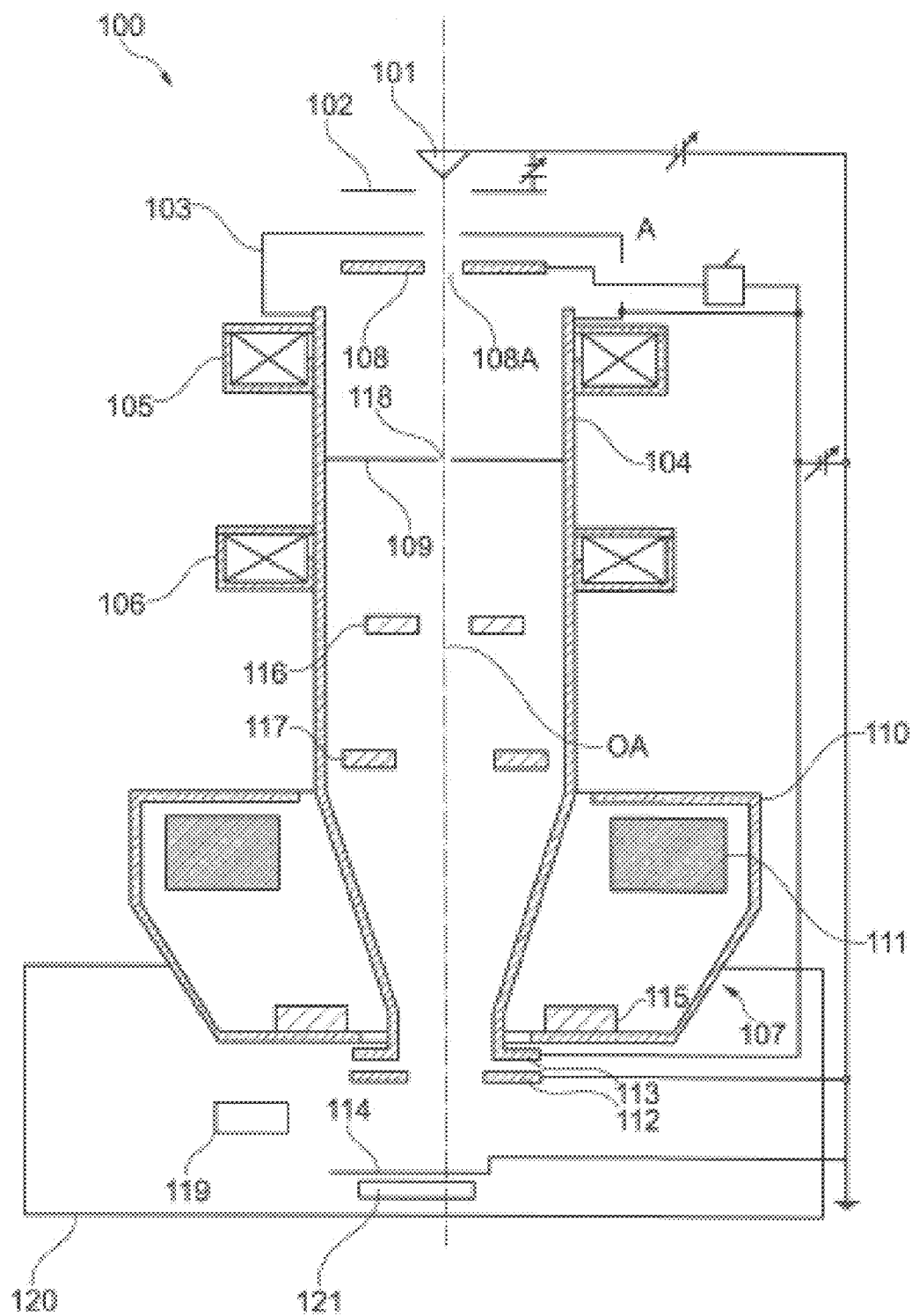
FIG. 1 shows a schematic illustration of a first particle beam apparatus in the form of a scanning electron microscope.

FIG. 1 shows a schematic illustration of an SEM 100. The SEM 100 has a first beam generator in the form of an electron source 101, which is embodied as a cathode. Furthermore, the SEM 100 is provided with an extraction electrode 102 and with an anode 103, which is placed onto one end of a beam guiding tube 104 of the SEM 100. By way of example, the electron source 101 is embodied as a thermal field emitter. However, the system described herein is not restricted to such an electron source. Rather, any electron source is utilizable.

Electrons emerging from the electron source 101 form a primary electron beam. The electrons are accelerated to the anode potential due to a potential difference between the electron source 101 and the anode 103. In the exemplary embodiment depicted here, the anode potential is 1 kV to 20 kV, e.g. 5 kV to 15 kV, in particular 8 kV, in relation to a ground potential of a housing of a sample chamber 120. However, alternatively it could be at ground potential.

Two condenser lenses, namely a first condenser lens 105 and a second condenser lens 106, are arranged at the beam guiding tube 104. Here, proceeding from the electron source 101 in the direction of a first objective lens 107, the first condenser lens 105 is arranged first, followed by the second condenser lens 106. Reference is explicitly made to the fact that further embodiments of the SEM 100 only have a single condenser lens.

A first aperture unit 108 is arranged between the anode 103 and the first condenser lens 105. Together with the anode 103 and the beam guiding tube 104, the first aperture unit 108 is at a high voltage potential, namely the potential of the anode 103, or it is connected to ground. The first aperture unit 108 has numerous first apertures 108A, of which one is depicted in FIG. 1. Each one of the numerous first apertures 108A has a different aperture diameter. By means of an adjustment mechanism (not depicted here), it is possible to set a desired first aperture 108A onto an optical axis OA of the SEM 100. A stationary second aperture unit 109 is arranged between the first condenser lens 105 and the second condenser lens 106.

The first objective lens 107 has pole pieces 110, in which a bore is formed. The beam guiding tube 104 is guided through this bore. Furthermore, a coil 111 is arranged in the pole pieces 110. An electrostatic retardation device is arranged in a lower region of the beam guiding tube 104. It has a single electrode 112 and a tube electrode 113. The tube electrode 113 is arranged at one end of the beam guiding tube 104, which faces an object 114. Together with the beam guiding tube 104, the tube electrode 113 is at the potential of the anode 103, while the single electrode 112 and the object 114 are at a lower potential in relation to the potential of the anode 103. In the present case, this is the ground potential of the housing of the sample chamber 120. In this manner, the electrons of the primary electron beam can be decelerated to a desired energy which is required for examining the object 114.

The SEM 100 furthermore has a scanning device 115, by means of which the primary electron beam can be deflected and scanned over the object 114. Here, the electrons of the primary electron beam interact with the object 114. As a result of the interaction, interaction particles and/or interaction radiation is/are produced, which is/are detected. In particular, electrons are emitted from the surface of the object 114—the so-called secondary electrons—or electrons of the primary electron beam are scattered back—the so-called backscattered electrons—as interaction particles.

A detector arrangement comprising a first detector 116 and a second detector 117 is arranged in the beam guiding tube 104 for detecting the secondary electrons and/or the backscattered electrons. Here, the first detector 116 is arranged on the source-side along the optical axis OA, while the second detector 117 is arranged on the object-side along the optical axis OA in the beam guiding tube 104. The first detector 116 and the second detector 117 are arranged offset from one another in the direction of the optical axis OA of the SEM 100. Both the first detector 116 and the second detector 117 each have a passage opening, through which the primary electron beam can pass. The first detector 116 and the second detector 117 are approximately at the potential of the anode 103 and of the beam guiding tube 104. The optical axis OA of the SEM 100 extends through the respective passage openings.

The second detector 117 serves to detect those electrons which emerge from the object 114 under a relatively large solid angle. These are primarily secondary electrons. By contrast, only a relatively small portion of electrons scattered back at the object 114—i.e. backscattered electrons—which have a relatively high kinetic energy compared to the secondary electrons when emerging from the object 114 are detected by the second detector 117 since the backscattered electrons are focused relatively close to the optical axis OA by the first objective lens 107 and they are therefore able to pass through the passage opening of the second detector 117. Therefore, the first detector 116 substantially serves to detect the backscattered electrons.

In a further embodiment of the particle beam apparatus, the first detector 116 can be embodied, additionally or alternatively, with a grid electrode (not depicted here). The grid electrode is arranged at the side of the first detector 116 directed toward the object 114. In respect of the potential of the beam guiding tube 104, the grid electrode has such a negative potential that only backscattered electrons with a high energy are able to pass through the grid electrode to the first detector 116. Additionally or alternatively, the second detector 117 has a grid electrode, which has an analogous embodiment to the aforementioned grid electrode of the first detector 116 and which has an analogous function.

The detection signals generated by the first detector 116 and the second detector 117 are used to generate an image or images of the surface of the object 114.

Reference is explicitly made to the fact that the apertures of the first aperture unit 108 and of the second aperture unit 109, as well as the passage openings of the first detector 116 and of the second detector 117 are depicted in exaggerated fashion. The passage openings of the first detector 116 and of the second detector 117 have a longest extent in the region of 1 mm to 5 mm. By way of example, they have a circular embodiment and a diameter in the region of 1 mm to 3 mm.

The second aperture unit 109 is configured as a pinhole aperture in the exemplary embodiment depicted here and it is provided with a second aperture 118 for the passage of the primary electron beam, which has an extent in the region of 5 µm to 500 µm, e.g. 35 µm. The second aperture unit 109 is embodied as a pressure stage aperture. It separates a first region, in which the electron source 101 is arranged and in which an ultra-high vacuum ($10^{-6}$ Pa to $10^{-10}$ Pa) prevails, from a second region, which has a high vacuum ($10^{-1}$ Pa to $10^{-6}$ Pa). The second region is the intermediate pressure region of the beam guiding tube 104, which leads to the sample chamber 120.

In addition to image generation, further examination methods can be carried out using the SEM 100. These include the so-called EBSD ("electron backscattered diffraction") method, in which diffraction patterns of scattered electrons are established. A further examination method is based on the detection of cathodoluminescence light, which emerges from the object 114 when the primary electron beam is incident on the object 114. Further examination methods include, for example, the examination by means of energy-dispersive x-ray spectroscopy (EDX) and the examination by means of wavelength-dispersive x-ray spectroscopy (WDX). For these further examination methods, provision is made of at least a third detector 119, which is arranged in the region of the sample chamber 120, for example between the beam guiding tube 104 and the object 114 or laterally from the object 114. In a further embodiment, provision is made for the third detector 119 to be arranged behind the single electrode 112—as seen from the electron source 101 in the direction of the object 114—and between the single electrode 112 and the object 114. In this embodiment, the detector 119 then has a passage opening for the primary electron beam, wherein the diameter of this passage opening is similar or identical to the diameter of the passage openings of the first detector 116 and of the second detector 117.

In further embodiments of the particle beam apparatus in the form of the SEM 100, provision can also be made of further third detectors, which can be used in addition to the already described detection methods (EBSD, detection of cathodoluminescence light, EDX and WDX), in particular also for the detection of the secondary electrons and/or backscattered electrons.

The SEM 100 has a fourth detector 121, which is arranged in the sample chamber 120. More precisely, the fourth detector 121 is arranged behind the object 114, as seen from the electron source 101 along the optical axis OA. The primary electron beam passes through the object 114 to be examined. When the primary electron beam passes through the object 114 to be examined, the electrons of the primary electron beam interact with the material of the object 114 to be examined. The electrons passing through the object 114 to be examined are detected by the fourth detector 121.

Figure 2:
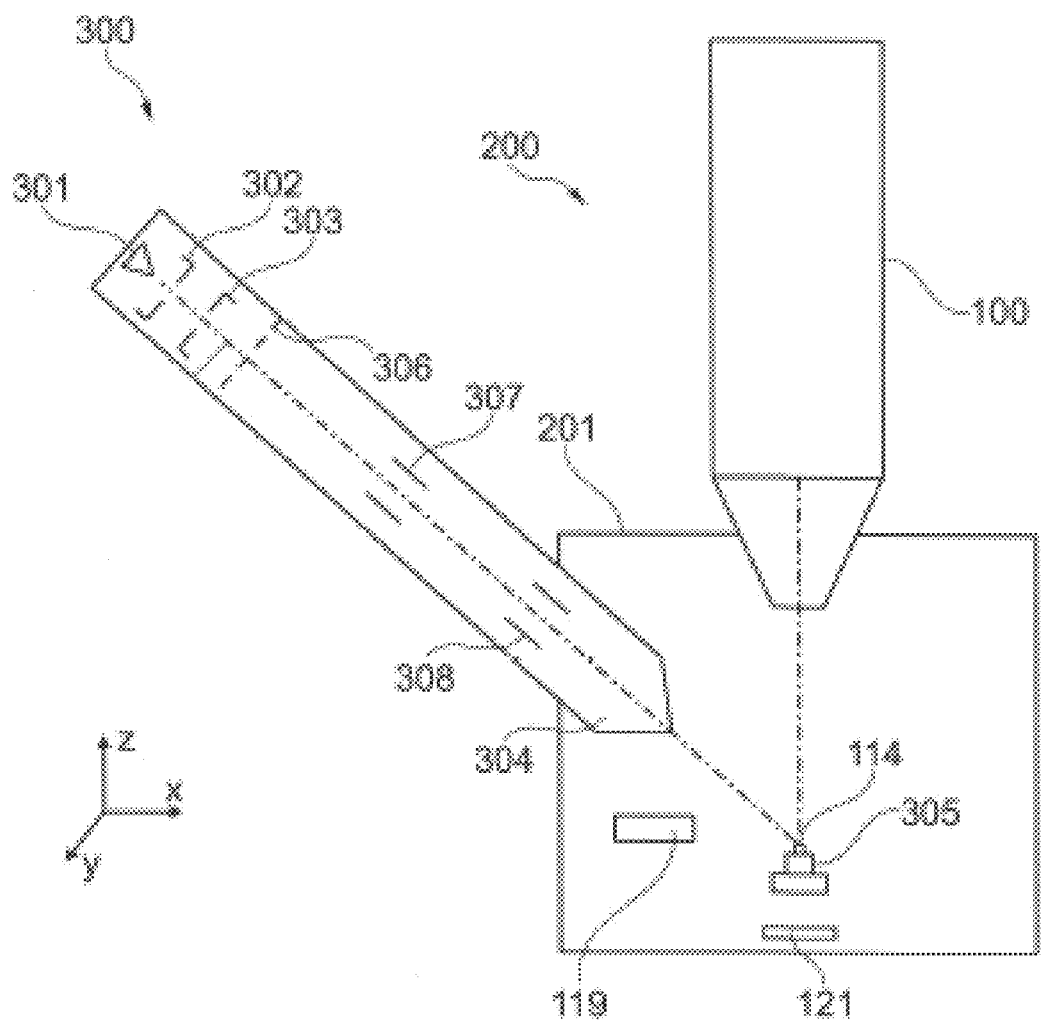
FIG. 2 shows a schematic illustration of a second particle beam apparatus comprising an electron beam column and comprising an ion beam column.

FIG. 2 shows a particle beam apparatus in the form of a combination apparatus 200. The combination apparatus 200 has two particle beam columns. Firstly, the combination apparatus 200 is provided with the SEM 100, as already depicted in FIG. 1, but without the sample chamber 120. Rather, the SEM 100 is arranged at a sample chamber 201. The SEM 100 serves to generate a first particle beam, namely the primary electron beam already described further above. Secondly, the combination apparatus 200 is provided with an ion beam apparatus 300, which is likewise arranged at the sample chamber 201.

The SEM 100 is arranged vertically in relation to the sample chamber 201. By contrast, the ion beam apparatus 300 is arranged inclined by an angle of approximately 50° in relation to the SEM 100. It has a second beam generator in the form of an ion beam generator 301. Ions, which form a second particle beam in the form of an ion beam, are generated by the ion beam generator 301. The ions are accelerated to a predeterminable potential by means of an extraction electrode 302. The second particle beam then reaches through ion optics of the ion beam apparatus 300, wherein the ion optics comprise a condenser lens 303 and an arrangement of further lenses 304, which form a second objective lens. The lenses 304 ultimately generate an ion probe, which is focused on the object 114 arranged on a sample holder 305.

An adjustable aperture 306, a first electrode arrangement 307 and a second electrode arrangement 308 are arranged above the lenses 304 (i.e. in the direction of the ion beam generator 301), wherein the first electrode arrangement 307 and the second electrode arrangement 308 are embodied as scanning electrodes.

The second particle beam is scanned over the surface of the object 114 by means of the first electrode arrangement 307 and the second electrode arrangement 308, wherein the first electrode arrangement 307 acts in a first direction and the second electrode arrangement 308 acts in a second direction, which is counter to the first direction. Using this, there is a scanning in e.g. the x-direction. The scanning in a y-direction perpendicular thereto is brought about by further electrodes (not depicted here), which are rotated by 90°, at the first electrode arrangement 307 and at the second electrode arrangement 308.

The distances depicted in FIG. 2 between the individual units of the combination apparatus 200 are depicted in exaggerated fashion in order to better depict the individual units of the combination apparatus 200.

Figure 3:
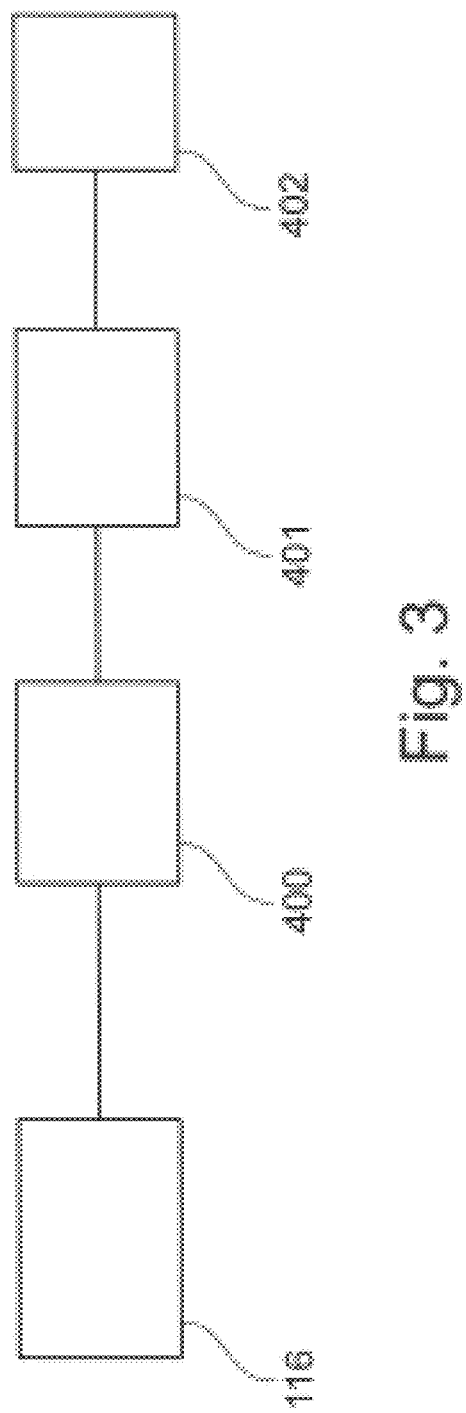
FIG. 3 shows a schematic illustration of a circuit of units for reading a detector.

FIG. 3 shows a schematic illustration of a circuit of units, which is used to read out the aforementioned four detectors 116, 117, 119 and 121. In FIG. 3, this is explained in an exemplary manner on the basis of the first detector 116. Corresponding circuits are also provided for the second detector 117, for the third detector 119 and for the fourth detector 121. The first detector 116 is connected to an analog-to-digital converter 400 by means of at least one first line. The analog-to-digital converter 400 converts analog signals from the first detector 116 into digital signals. The analog-to-digital converter 400 is connected, in turn, to a computer 401 by a second line. The digital signals are transmitted to the computer 401 by way of the second line. The computer 401 is connected, in turn, to a screen 402.

Below, the design of the four aforementioned detectors 116, 117, 119 and 121 is discussed on the basis of FIGS. 4 and 5. The fourth detector 121, which is arranged in the sample chamber 120 (cf. FIG. 1) or in the sample chamber 201 (cf. FIG. 2), is described first using FIG. 4. The third detector 119 basically has an identical design to the fourth detector 121 when the third detector 119 is arranged in the sample chamber 120 (cf. FIG. 1) or laterally next to the optical axis OA in the sample chamber 201 (cf. FIG. 2)—i.e. laterally next to the primary electron beam. The following statements then apply analogously to the third detector 119.

The fourth detector 121 has a detection surface, on which a first pixel field 407 is arranged. Furthermore, the fourth detector 121 is provided with a first preamplifier unit 403 and with a first control device 404. The first pixel field 407 has a multiplicity of pixels. By way of example, the first pixel field 407 is provided with 1028×1028 pixels. However, for a simplified illustration, only 30 pixel fields are plotted in FIG. 4. As stated, the first pixel field 407 can have many more pixels. Each pixel is embodied as a detection unit, for example in the form of a semiconductor element, in particular as a PIN diode or avalanche diode. Each individual pixel of the first pixel field 407 is respectively connected to a preamplifier of the first preamplifier unit 403 by way of first feed lines 405. Accordingly, in this embodiment, the first preamplifier unit 403 has the same number of preamplifiers (namely V1 to V30) as pixels are present in the first pixel field 407. The first preamplifier unit 403 is connected to the first control device 404 by way of second feed lines 406. The first control device 404 is connected to the computer 401 and to the analog-to-digital converter 400.

Figure 4:
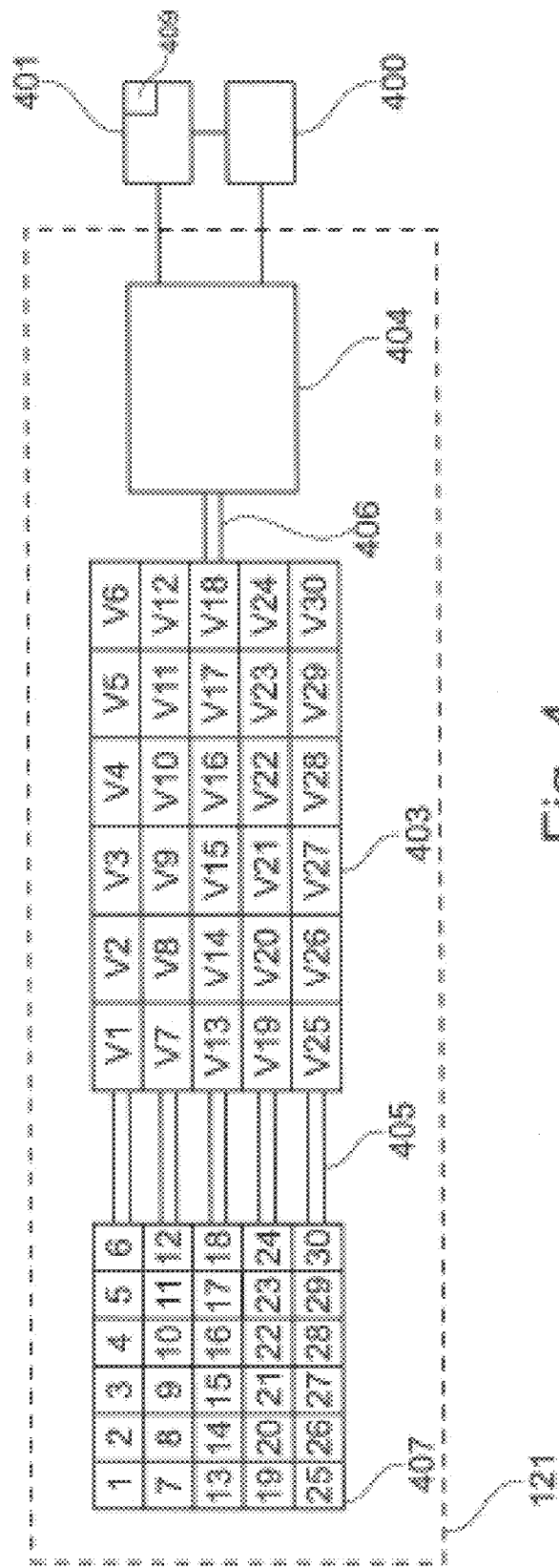
FIG. 4 shows a schematic illustration of a design of a detector.
Figure 5:
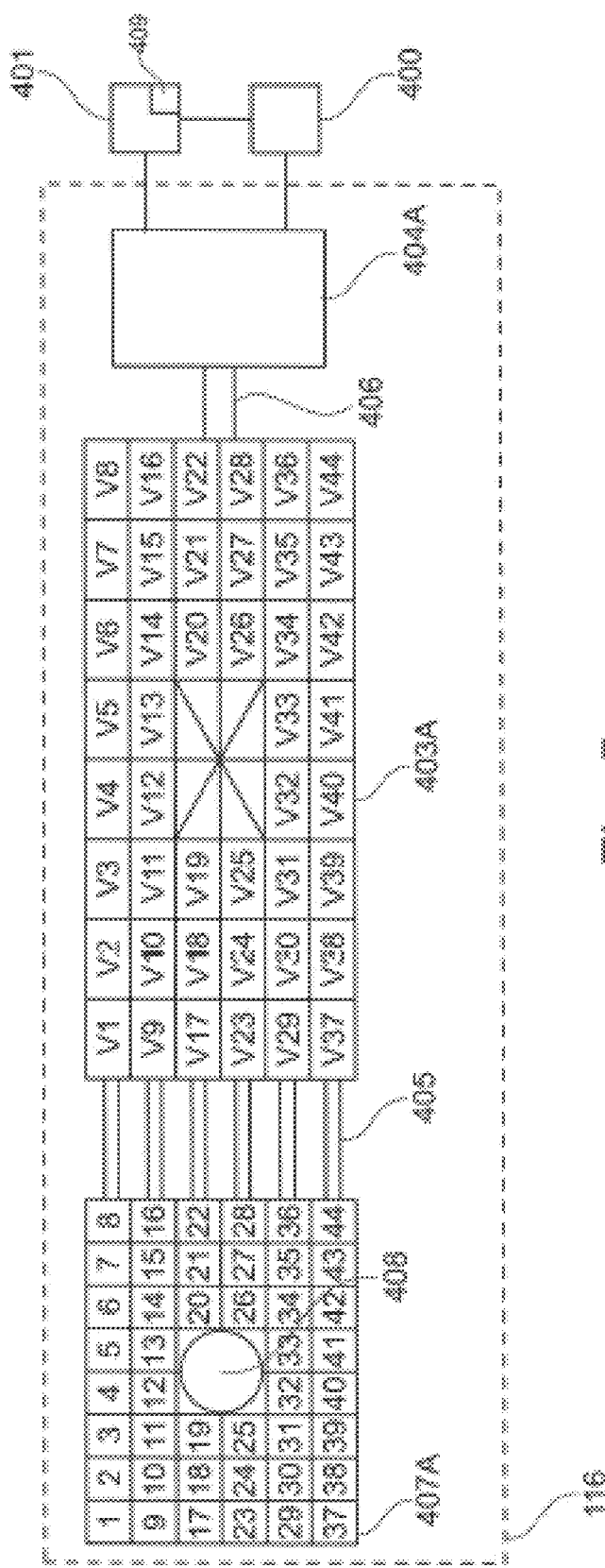
FIG. 5 shows a schematic illustration of a design of a further detector.

FIG. 5 shows an embodiment of the first detector 116. In principle, the second detector 117 has an identical design to the first detector 116, and so the subsequent statements also apply to the second detector 117. If the third detector 119 is arranged in the sample chamber 120 (cf. FIG. 1) or in the sample chamber 201 (cf. FIG. 2) behind the single electrode 112—as seen from the electron source 101 in the direction of the object 114—and between the single electrode 112 and the object 114, then the third detector 119 has an identical design to the first detector 116. In particular, it has a passage opening, as already explained above. The following statements then apply analogously to the third detector 119. The first detector 116 has a detection surface, on which a second pixel field 407A is arranged. Furthermore, the first detector 116 is provided with a second preamplifier unit 403A and with a second control device 404A. The second pixel field 407A has a multiplicity of pixels. By way of example, the second pixel field 407A is provided with 1028×1028 pixels. However, for a simplified illustration, only 44 pixel fields are plotted in FIG. 5. However, the second pixel field 407A can have any suitable number of pixels. In the first detector 116, each pixel is also embodied as a detection unit, for example in the form of a semiconductor element, in particular as a PIN diode or avalanche diode. Each individual pixel of the second pixel field 407A is respectively connected to a preamplifier of the second preamplifier unit 403A by way of the first feed lines 405. Accordingly, in this embodiment, the second preamplifier unit 403A has the same number of preamplifiers (namely V1 to V44) as pixels are present in the second pixel field 407A. The second preamplifier unit 403A is connected to the second control device 404A by way of the second feed lines 406. The second control device 404A is connected to the computer 401 and to the analog-to-digital converter 400. In contrast to the embodiment in accordance with FIG. 4, the second pixel field 407A still additionally has a passage opening 408 for the primary electron beam.

The aforementioned computer 401 has a processor, in which a computer program product is loaded which, when executed, causes the SEM 100 in accordance with FIG. 1 or the combination apparatus 200 in accordance with FIG. 2 to be controlled in such a way that a method according to the system described herein is carried out.

Below, the method according to the system described herein is explained in more detail on the basis of exemplary embodiments. In one exemplary embodiment, information about the object is established using the SEM 100 or the combination apparatus 200 and it is then stored in a data memory 409 of the computer 401. In a further exemplary embodiment, the information is already known, for example from preliminary examinations with reference objects using further examination devices, e.g. particle beam apparatuses, and it is stored in the data memory 409 of the computer 401. In both exemplary embodiments, the information contains information about the interaction behavior of the primary electron beam or of the ion beam with the material of the object 114 and/or about the solid angle regions, in which the interaction particles propagate after the generation thereof and/or into which the interaction radiation is emitted after the generation thereof. These are characteristic for the properties of the object 114, which were already explained further above. A further exemplary embodiment assumes that solid angle regions, in which the interaction particles propagate after the generation thereof and/or into which the interaction radiation is emitted after the generation thereof, are dependent on setting parameters of the particle beam apparatus, for example in the form of the SEM 100 in accordance with FIG. 1 or of the combination apparatus 200 in accordance with FIG. 2. As already mentioned above, this exemplary embodiment assumes that it is possible to decisively influence and control the behavior of the interaction particles and/or of the interaction radiation on account of the setting parameters and independently of the nature of the object 114 such that the aforementioned solid angle regions are determinable, e.g. by means of a calculation. The information about possible solid angle regions as a function of the setting parameters were e.g. determined by calculation and stored in the data memory 409.

Using the information stored in the data memory 409 in the exemplary embodiments, it is possible to identify regions on the object 114, which appear to be particularly interesting, for a further analysis.

Figure 6:
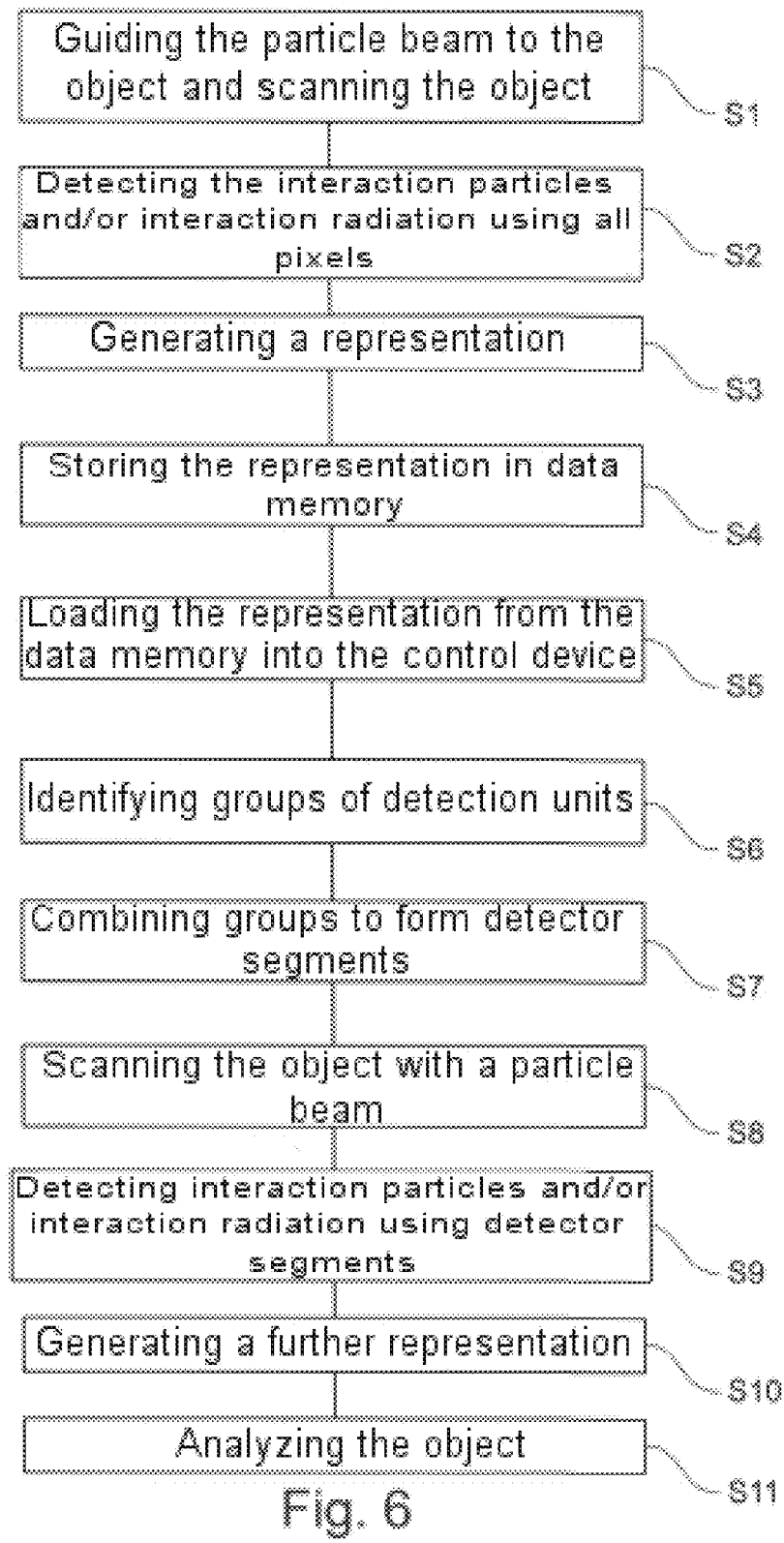
FIG. 6 shows a schematic illustration of an operational sequence of an embodiment of the method according to the system described herein.

FIG. 6 schematically shows a flowchart of an exemplary embodiment of the method according to the system described herein, which is carried out using the SEM 100 in accordance with FIG. 1 or the combination apparatus 200 in accordance with FIG. 2. In this exemplary embodiment, information about the interaction behavior of the object 114 with the particle beam is obtained when carrying out the method itself, as will be explained below.

In a first method step S1, the particle beam is guided to the object 114 and scanned over the surface of the object 114. In the SEM 100 in accordance with FIG. 1, the particle beam is the primary electron beam. If the method according to the system described herein is used in the combination apparatus 200 in accordance with FIG. 2, this particle beam is, for example, the primary electron beam of the SEM 100 or the ion beam of the ion beam apparatus 300.

Then, in a further method step S2, interaction particles and/or interaction radiation, which is/are produced due to the interaction of the primary electron beam and/or ion beam with the material of the object 114, is/are detected. Both in the embodiment of the particle beam apparatus in the form of the SEM 100 depicted in FIG. 1 and in the embodiment of the particle beam apparatus in the form of the combination apparatus 200 depicted in FIG. 2, the interaction particles and/or the interaction radiation is detected using the first detector 116, using the second detector 117, using the third detector 119 and/or using the fourth detector 121. More precisely, backscattered electrons are substantially detected using the first detector 116 or using the third detector 119, when the third detector 119 is arranged in the sample chamber 120 (cf. FIG. 1) or in the sample chamber 201 (cf. FIG. 2) between the single electrode 112 and the object 114 along the optical axis OA, wherein the third detector 119 has a passage opening, as already explained above. Secondary electrons are substantially detected using the second detector 117. If the third detector is arranged in the sample chamber 120 (cf. FIG. 1) or in the sample chamber 201 (cf. FIG. 2) laterally in relation to the optical axis OA and if it is not provided for the passage of the primary electron beam, then the third detector 119 serves, for example, to detect interaction particles, when these interaction particles are scattered in the sample chamber 120 (cf. FIG. 1) or in the sample chamber 201 (cf. FIG. 2), or to detect interaction radiation in the form of x-ray radiation or cathodoluminescence radiation. The fourth detector 121 substantially serves to detect scattered electrons passing through the object 114. In order to be able to detect scattered electrons passing through the object 114 in the exemplary embodiment of FIG. 2, the sample holder 305 is moved and rotated using movement devices (not depicted here) in such a way that scattered electrons passing through the object 114 are able to reach the fourth detector 121 and are able to be detected by the fourth detector 121.

The method step S2 is explained specifically in more detail below by the detection of interaction particles by means of the fourth detector 121. Corresponding statements apply to the detection of interaction particles and/or interaction radiation using the further detectors.

The detection of interaction particles, in particular the electrons of the primary electron beam passing through the object 114, using the fourth detector 121 is carried out in method step S2 in such a way that initially all pixels of the first pixel field 407 are taken into account in the detection. More precisely, detection signals from all pixels in the first pixel field 407 of the fourth detector 121 are taken into account. Each detection signal from each pixel in the first pixel field 407 is amplified by the preamplifier of the first preamplifier unit 403 assigned to the pixel; subsequently, said detection signal is read by the first control unit 404 and then forwarded to the analog-to-digital converter 400. After conversion of the signals into digital signals, the latter are forwarded to the computer 401. The read detection signals are now used to generate a representation of the object 114 (method step S3). When the detection signals from the fourth detector 121 are considered, the representation is, for example, a first diffraction image of the object 114. By contrast, if the first detector 116, the second detector 117 and/or the third detector 119 are used to detect the interaction particles/interaction radiation and generate the representation, then the representation is, for example, an intensity distribution of the detection signals at the point of incidence of the interaction particles/interaction radiation on the pixels in the pixel field 407.

In a further method step S4, the representation established thus is stored in the data memory 409 of the computer 401. In an in turn further method step S5, the representation is loaded from the data memory 409 into the control device 404.

In a further method step S6, groups of pixels, i.e. groups of detection units, which can be combined to form detector segments are identified. In the method according to the system described herein, this can be carried out firstly using the computer 401 or using the control device 404. Both ways, i.e. firstly using the computer 401 and secondly using the control device 404, are explained below.

The way using the control device 404 is explained first. By way of example, in the representation of the object 114 now loaded into the control device 404, it is possible to identify and locally set regions with a high contrast and/or regions with a high intensity using image recognition software running on the control device 404. These regions with a high contrast and/or regions with a high intensity are generally those regions that are characteristic for the material of interest on the object and that should therefore be examined in more detail and/or imaged. In particular, it is desirable to examine and/or image these again.

The way using the computer 401 is, in principle, analogous. The information loaded into the control device 404 or the information stored in the data memory 409 is loaded into a processor of the computer 401. Now it is also possible here, for example, to identify and locally set regions with a high contrast and/or regions with a high intensity in the representation of the object 114 loaded into the processor. The identification of these regions can be carried out e.g. visually on the screen 402 by a user or e.g. in an automated manner by means of image recognition software.

Figure 7:
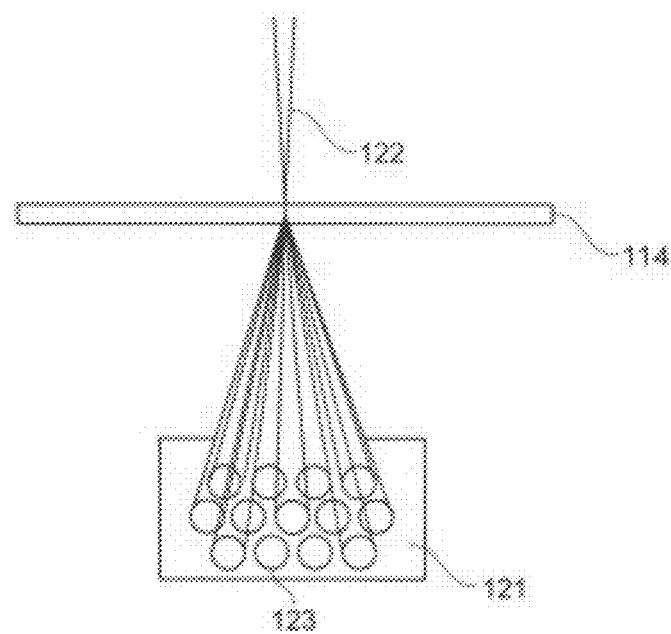
FIG. 7 shows a schematic illustration of a generation of an STEM image.
Figure 8:
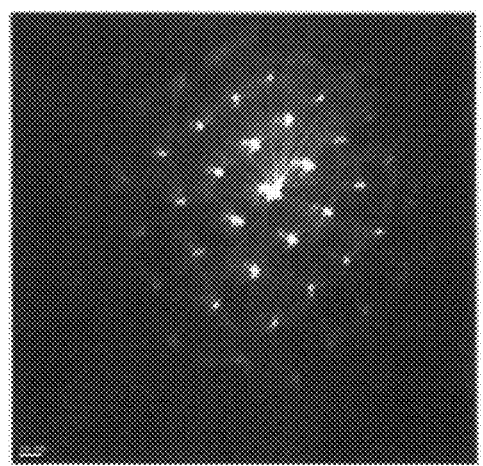
FIG. 8 shows a schematic illustration of a diffraction pattern.

The method step S6 is explained in more detail in an exemplary manner with reference to FIGS. 7 and 8 for both types of use (that is to say firstly with the computer 401 and secondly with the control device 404). FIG. 7 shows the object 114, through which the primary electron beam 122 passes, in a schematic illustration. When the primary electron beam 122 passes through the object 114, the electrons of the primary electron beam 122 interact with the material of the object 114 and they are scattered. The electrons passing through the object 114 are detected by the fourth detector 121. Diffraction patterns with a distribution of intensity maxima 123 that is typical for diffraction patterns are produced, which is once again depicted in FIG. 8. Identifying and combining pixels to form detector segments is carried out in such a way, for example, that the detector segments detect interaction particles from these identified regions in a targeted manner. By way of example, in the exemplary embodiment depicted in FIG. 7, these are the intensity maxima 123. All pixels, which detect a single intensity maximum 123 and which are arranged in the solid angle region in which the interaction particles of an intensity maximum 123 propagate, are identified and combined to form a single detector segment.

The combination of groups of pixels to form the individual detector segments is carried out in method step S7. By way of example, pixels 1, 2, 7 and 8 are combined to form a first detector segment, pixels 5, 6, 11 and 12 are combined to form a second detector segment, pixels 19, 20, 25 and 26 are combined to form a third detector segment and pixels 23, 24, 29 and 30 are combined to form a fourth detector segment after the identification thereof. In this embodiment, provision is made to draw together mutually adjacent detection units in the form of the pixels to form a detector segment. However, the system described herein is not restricted to always combine adjacent pixels to form detector segments. This is because in a further embodiment of the system described herein, provision is additionally or alternatively made of assigning to a single detector segment detection units in the form of pixels which are respectively spaced apart from one another and which do not adjoin one another locally. By way of example, pixels 1, 2, 25 and 26 could be drawn together to form a detector segment for this further embodiment. As already explained above, the form of the individual detector segments can always be selected in a suitable and free manner. By way of example, at least one detector segment can have a square, circular ring-shaped, circular segment-shaped, circular or cross-shaped embodiment.

When combining the groups of pixels to form detector segments, information about both the identified groups and the individual formed detector segments is loaded into the control devices of the respective detectors. In the exemplary embodiment in respect of the fourth detector 121 explained above, this is the first control device 404.

Subsequently, the particle beam is guided to the object 114 and the object 114 is scanned by the particle beam in a further method step S8. In the SEM 100 in accordance with FIG. 1, this is the primary electron beam. If the method according to the system described herein is used in the combination apparatus 200 in accordance with FIG. 2, this particle beam is, for example, the primary electron beam of the SEM 100 or the ion beam of the ion beam apparatus 300.

In a further method step S9, the interaction particles and/or the interaction radiation, which is/are produced due to the interaction of the primary electron beam and/or ion beam with the material of the object 114, is/are detected again. Both in the embodiment of the particle beam apparatus in the form of the SEM 100 depicted in FIG. 1 and in the embodiment of the particle beam apparatus in the form of the combination apparatus 200 depicted in FIG. 2, the interaction particles and/or the interaction radiation is detected using the first detector 116, using the second detector 117, using the third detector 119 and/or using the fourth detector 121. Since the method step S9 is based on the method step S2, what is said above also applies here. However, there is a quite essential difference between the method step S9 and the method step S2. Now, it is no longer all pixels of the individual aforementioned detector units in the form of pixels that are taken into account, but only the signals of the formed detector segments. The method step S9 is explained in more detail below on the basis of the detection using the fourth detector 121, which was likewise used for the more detailed explanation of method step S2.

The electrons of the primary electron beam passing through the object 114 are once again detected by the fourth detector 121. However, it is now no longer the detection signals from all detection units in the form of pixels of the fourth detector 121 that are read; rather, it is only the detector segment signals of the detector segments that are amplified by preamplifiers of the first preamplifier unit 403 and read by the first control device 404. Accordingly, a first detector segment signal from the first detector segment consisting of pixels 1, 2, 7 and 8, a second detector segment signal from the second detector segment consisting of pixels 5, 6, 11 and 12, a third detector segment signal from the third detector segment consisting of pixels 19, 20, 25 and 26 and a fourth detector segment signal from the fourth detector segment consisting of pixels 23, 24, 29 and 30 are read. The first detector segment signal is provided by the first detector segment when at least one detection unit in the form of pixels 1, 2, 7 and 8 detects, for example, the electrons passing through the object 114. The second detector segment signal is provided by the second detector segment when at least one detection unit in the form of pixels 5, 6, 11 and 12 detects, for example, the electrons passing through the object 114. The third detector segment signal is provided by the third detector segment when at least one detection unit in the form of pixels 19, 20, 25 and 26 detects, for example, the electrons passing through the object 114. The fourth detector segment signal is provided by the fourth detector segment when at least one detection unit in the form of pixels 23, 24, 29 and 30 detects, for example, the electrons passing through the object 114.

Then, a further representation of the object 114 is generated by means of the read detector segment signals (method step S10). This further representation of the object 114 using the read detector segment signals is generally an image of the object 114, wherein the read detector segment signals are used to generate the image. In the explained exemplary embodiment relating to the fourth detector 121, the further representation of the object 114 is accordingly generated from the first detector segment signal, the second detector segment signal, the third detector segment signal and the fourth detector segment signal. However, reference is explicitly made to the fact that it is not necessary to use all of the detector segment signals. Rather, the system described herein provides for an arbitrary number of detector segment signals from one or more detector segments to be sufficient for generating the further representation. The object 114 is then analyzed on the basis of the further representation (method step S11).

Figure 6A:
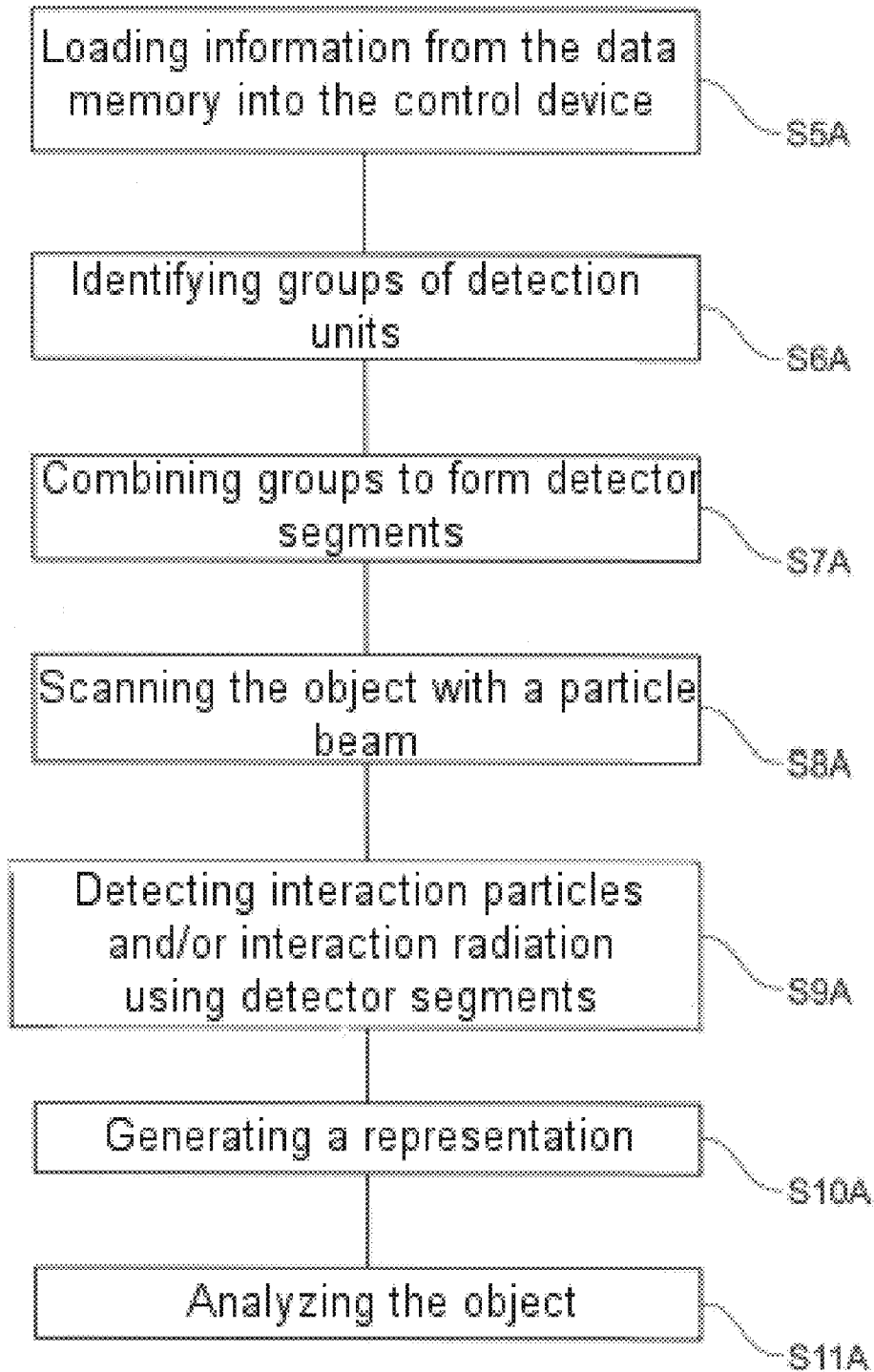
FIG. 6A shows a schematic illustration of an operational sequence of a further embodiment of the method according to the system described herein.

FIG. 6A schematically shows a flowchart of a further exemplary embodiment of the method according to the system described herein, which is carried out using the SEM 100 in accordance with FIG. 1 or the combination apparatus 200 in accordance with FIG. 2. The exemplary embodiment of FIG. 6A is based on the exemplary embodiment of FIG. 6. Therefore, reference is initially made to the explanations above.

In contrast to the exemplary embodiment of FIG. 6, the exemplary embodiment in FIG. 6A starts with the method step S5A. In method step S5A, information is loaded into the control device 404 or 404A from the data memory 409, which information was, for example, established by measurements of known reference objects (which are also referred to as calibration objects) and stored in the data memory 409. In particular, the information comprises the interaction behavior of the particle beam with the material of the object 114 and/or the solid angle regions, in which the interaction particles propagate after the generation thereof and/or into which the interaction radiation is emitted after the generation thereof. As already mentioned above, this information is characteristic for the properties of the object 114, which were already explained above. On the basis of this information, it is possible to identify reBions on the object 114 which appear of particular interest for a further analysis. The measurements on the reference object can be undertaken, for example, by measurements which have the method steps S1 to S4 of the exemplary embodiment in accordance with FIG. 6.

In a further exemplary embodiment, provision is made for undertaking method steps S1 to S4 not on the actual object 114, but rather on a reference object or calibration object.

As already mentioned above, the information, which is loaded into the data memory 409, can also be calculated. This will be explained in more detail below. Thus, provision is made of obtaining information about the interaction behavior of the particle beam with a specific material of the object 114 by simulating the scattering behavior of the particle beam with the specific material of the object 114. By way of example, the particle beam is the primary electron beam of the SEM 100 or the ion beam of the ion beam apparatus 300. This exemplary embodiment is initially based on the consideration that the object 114 can have different materials, e.g. a metal and/or carbon. If one of these materials is of particular interest (that is to say the aforementioned specific material), then the region of the object 114 containing the specific material should be examined in more detail. If the physical properties of the specific material of the object 114 are known, it is possible to calculate the solid angle regions into which the particle beam is e.g. scattered. Then, it is thus possible to identify the groups of pixels (i.e. groups of detection units) which are predominantly hit by the scattered particle beam. These groups can then be combined to form detector segments.

In a further method step S6A, groups of pixels which can be combined to form detector segments are identified. By way of example, it is possible to generate a representation of the object 114 by means of the primary electron beam. Regions of the object 114 with a high contrast and/or regions of high intensity are identified and spatially fixed. Furthermore, these regions are compared to the information loaded into the control device 404. If the identified and spatially fixed regions have characteristics (for example contrast and/or intensity) which correspond to characteristics of the information loaded into the control device 404, then these are regions which are characteristic for a material of interest on the object 114 and which should therefore be examined in more detail and/or which should be imaged. In particular, it is desirable to examine and/or image these again. The identification of these regions can be carried out e.g. visually on the screen 402 by a user or e.g. in an automated manner by means of image recognition software. Identifying and combining pixels to form detector segments is then carried out in such a way that the detector segments detect interaction particles from these identified regions in a targeted manner.

Combining the groups of pixels to form the individual detector segments is carried out in method step S7A, wherein all explanations made in respect of method step S7 of the exemplary embodiment in FIG. 6 likewise apply here. When combining the groups of pixels to form detector segments, information about both the identified groups and the individual formed detector segments is loaded into the control devices of the respective detectors. In the exemplary embodiment in respect of the fourth detector 121 explained above, this is the first control device 404.

Subsequently, the particle beam is guided to the object 114 and the object 114 is scanned in a further method step S8A. In the SEM 100 in accordance with FIG. 1, this is the primary electron beam. If the method according to the system described herein is used in the combination apparatus 200 in accordance with FIG. 2, this particle beam is, for example, the primary electron beam of the SEM 100 or the ion beam of the ion beam apparatus 300. In a further method step S9A, the interaction particles and/or the interaction radiation, which is/are produced due to the interaction of the primary electron beam and/or ion beam with the material of the object 114, is/are detected. Both in the embodiment of the particle beam apparatus in the form of the SEM 100 depicted in FIG. 1 and in the embodiment of the particle beam apparatus in the form of the combination apparatus 200 depicted in FIG. 2, the interaction particles and/or the interaction radiation is detected using the first detector 116, using the second detector 117, using the third detector 119 and/or using the fourth detector 121. Now, it is only still the signals of the formed detector segments that are taken into account. The method step S9A is explained in more detail below by the detection using the fourth detector 121. The electrons of the primary electron beam passing through the object 114 are once again detected by the fourth detector 121. However, it is now no longer the detection signals from all detection units in the form of pixels of the fourth detector 121 that are read; rather, it is only the detector segment signals of the detector segments that are amplified by preamplifiers of the first preamplifier unit 403 and read by the first control device 404. Here too, all explanations in relation to the method step S9 in FIG. 6 apply analogously. Then, a representation of the object 114 is generated by means of at least one of the read detector segment signals (method step S10A). This representation of the object 114 using the read detector segment signal or the read detector segment signals is generally an image of the object 114, wherein the read detector segment signals are used to generate the image. The object 114 is then analyzed on the basis of the further representation (method step S11A).

The method according to the system described herein, in particular all exemplary embodiments of the method explained above, can be used in any type of examination of objects with charged particles. In particular, the method according to the system described herein can be used in the analysis of Kikuchi bands. By way of example, the EBSD method is used to analyze the crystallographic orientation of materials. By way of example, for detection purposes, the third detector 119 is used as an EBSD detector in this method. The third detector 119 detects electrons scattered back from the object 114 and generates corresponding detection signals. A diffraction pattern can be generated on the basis of the detection signals. The diffraction pattern comprises information about Kikuchi bands, which correspond to lattice diffraction planes of the object 114. By way of example, the method according to the system described herein is now applied in such a way in the analysis of the Kikuchi bands that detection units in the form of pixels are identified, which are arranged in the direct vicinity of characteristic Kikuchi bands, wherein the Kikuchi bands are part of a structure with a material of interest and/or they correspond to a specific crystal orientation of interest of the object 114. By way of example, a single detector segment is used to represent the object 114 (method step S10 or S10A). In particular, an image of the structure is generated.

The method according to the system described herein can also be used in the analysis of the object 114 by means of the transmission Kikuchi diffraction method (referred to as TKD method below). In the TKD method, electrons of the primary electron beam are guided to the object 114 which is thin enough to be transparent to the electrons of the primary electron beam. Expressed in other words, the electrons of the primary electron beam are transmitted through the object 114. In the process, the object 114 is arranged tilted slightly away from the third detector 119 at an angle of up to 20° or 30°. Scattered and transmitted electrons of the primary electron beam emerge on the lower side of the object 114 and they are detected by the third detector 119. The Kikuchi diffraction pattern has intensity maxima, around which detection units in the form of pixels are identified and combined to form detector segments. In this respect, reference is made in an exemplary manner to the explanations relating to FIGS. 7 and 8, which apply here analogously. Here too, the detector segment signal of a single detector segment is used, for example, for representing the object 114 (method step S10 or S10A). In particular, an image of a structure of interest of the object 114 is generated. This image is used for analyzing the object 114.

The method steps of the embodiment of the method according to the system described herein are substantially described with reference to the fourth detector 121. Reference is once again explicitly made to the fact that the method according to the system described herein can be used in every detector of the particle beam apparatuses explained above.

The method according to the system described herein can also be used when generating a three-dimensional representation of the object 114. By way of example, the first detector 116 is used to generate a three-dimensional representation of the object 114. Alternatively or additionally thereto, the third detector 119 is used for this purpose when the third detector 119 is arranged in the sample chamber 120 (cf. FIG. 1) or in the sample chamber 201 (cf. FIG. 2) directly behind the single electrode 112—as seen from the electron source 101 in the direction of the object 114—and between the single electrode 112 and the object 114. In this case, as already explained above, the third detector 119 has a passage opening for the primary electron beam. By way of example, four detector segments of the first detector 116 are formed by means of the method according to the system described herein. By way of example, the four detector segments are selected in such a way that these are arranged symmetrically about the optical axis OA of the SEM 100. Each one of the four detector segments generates detector segment signals, which are respectively used for the image generation. Respectively one image of the object 114 is generated by each one of the detector segments such that a total of four images is generated by means of the first detector 116 or the third detector 119. Using the four generated images, gradients along a first axis (e.g. an x-axis) and along a second axis (e.g. a y-axis) are determined for the surface of the object 114. A grid of profiles, which can be assembled to form a three-dimensional model of the object 114, is obtained by integrating the gradients along the first axis and the second axis.

Figure 9:
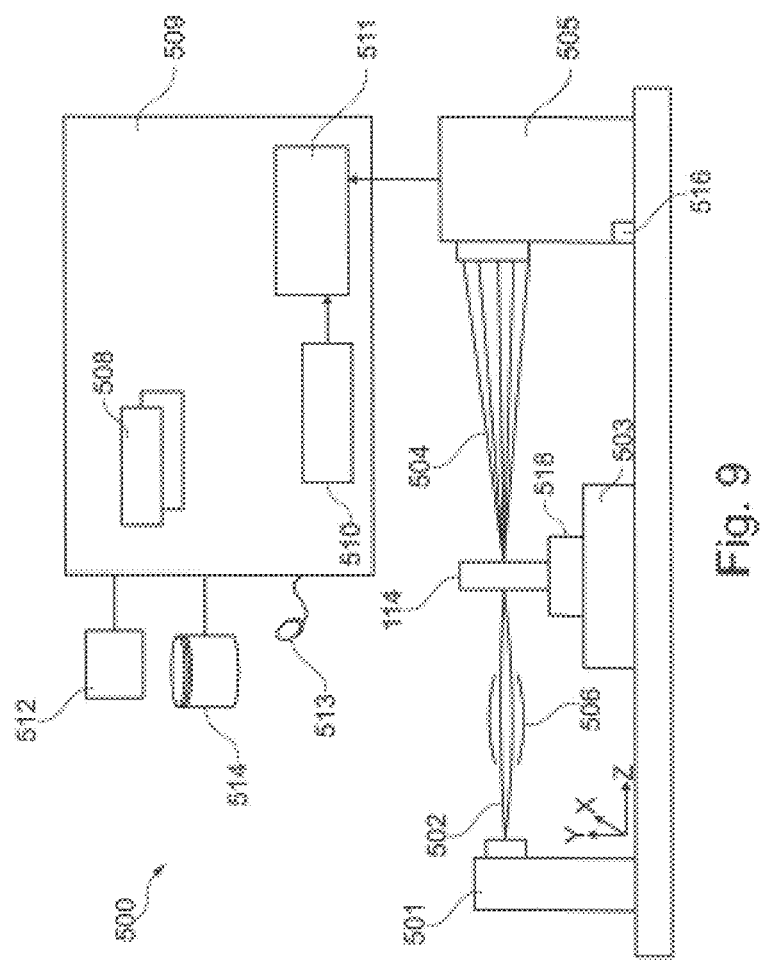
FIG. 9 shows a schematic illustration of an x-ray beam device.

FIG. 9 shows a schematic illustration of an x-ray beam device 500 in the form of an x-ray microprobe which can be used for the embodiments of the method according to the system described herein. The x-ray beam device 500 has a generator system 501 for x-rays—i.e. an x-ray source—which generates x-rays 502. Furthermore, the x-ray beam device 500 comprises a scanning stage 503 with an object holder 518 for holding the object 114. The scanning stage 503 will be discussed in more detail below.

In some exemplary embodiments, the generator system 501 for x-rays has integrated filters for filtering the x-rays 502. Moreover, a collimator 506 in the form of a zone plate is arranged between the generator system 501 for x-rays and the object 114 in the x-ray beam device 500. The collimator 506 focuses the x-rays 502 and generates an x-ray probe at the location of the object 114.

When the object 114 is irradiated by the x-rays 502, x-ray photons are transmitted through the object 114. These transmitted x-ray photons form transmitted x-rays 504, which are detected by a detector system 505. In some exemplary embodiments, use is made of an objective lens to generate an image of the x-ray probe on the detector system 505.

When the x-rays 502 pass through the object 114, the x-rays 502 interact with the material of the object 114 and the x-rays can be scattered. The x-rays 504 transmitted through the object 114 are detected by the detector system 505. Diffraction patterns are produced at the detector system 505 with a distribution of intensity maxima that is typical for diffraction patterns, similar to what is already presented in FIG. 7 using the example of electron beams. Identifying (method step 6) and combining (method step 7) pixels of the detector system 505 to form detector segments is carried out in such a way, for example, that the detector segments detect interaction radiation from these identified regions in a targeted manner. By way of example, these would be intensity maxima, similar to the exemplary embodiment depicted in FIG. 7. All pixels, which detect a single intensity maximum and which are arranged in the solid angle region in which the interaction radiation of an intensity maximum propagates, are identified and combined to form a single detector segment.

In this exemplary embodiment of the x-ray beam device 500, the detector system 505 is embodied like, for example, the fourth detector 121, which was explained in more detail by means of FIG. 4. Accordingly, reference is made here to all explanations in respect of FIG. 4, which also apply to the detector system 505. In the detector system 505, the individual pixels can be embodied as scintillation units, which serve to provide evidence for the transmitted x-rays 504. However, if the individual pixels are embodied as semiconductor elements, it is also possible for these to detect the transmitted x-rays 504 directly.

After the pixels, i.e. the detection units, where identified in method step 6 and the pixels, i.e. the detection units, of the detector system 505 were combined to form one or more detector segments in method step 7, the information about both the identified groups of pixels and the individual formed detector segments is loaded into a third control device 516 of the detector system 505.

Subsequently, the x-ray beam 502 is guided to the object 114 and the object 114 is scanned in the further method step S8. In the x-ray beam device 500 in the form of the x-ray microprobe described here, scanning is brought about by a movement. By way of example, scanning is brought about by moving the object 114 in relation to the stationary x-ray beam 502. To this end, the object stage, on which the object 114 is arranged, is embodied as a scanning stage 503, as already explained above. The scanning stage 503 has a movable embodiment in at least three translational directions, which e.g. are oriented perpendicular to one another. Additionally, the scanning stage 503 can have an embodiment that is rotatable about a first axis of rotation and/or about a second axis of rotation. The scanning stage 503 can scan the object 114 in relation to the stationary x-ray beam 502. The scanning stage 503 is moved from scanning point to scanning point. At least one detector segment of the detector system 505 detects a detection signal at each scanning point in accordance with the method step S9. An image of the object 114 is constructed by means of the detection signals detected at the individual scanning points. The detection signal detected for a scanning point can additionally be stored in a data memory 514 of a computer system 509. A display unit 512 can depict an image of the object 114 by means of the detected detection signals at each scanning point, in accordance with method step S10. Therefore, the object 114 can be analyzed using the detection signal at each scanning point, as is presented in method step 11. The method steps S9 to S11 are carried out analogously, as is described above using the example of the fourth detector 121. Here, the third control device 516 of the detector system 505 corresponds to the first control device 404 of the fourth detector 121. Furthermore, the computer system 509, which has an analog-to-digital converter 511, a controller 510, the data memory 514, the display unit 512, an input unit 513 and interface applications 508, corresponds to the computer 401 in FIG. 4.

Hence, the method according to the system described herein, which is explained in more detail on the basis of FIGS. 6 and 6A, can likewise be carried out using the x-ray beam device 500. However, in the x-ray beam device 500, the data memory 514 is used as data memory and the x-rays 502 are used as examination beam. All explanations in respect of FIGS. 6 and 6A also apply to the x-ray beam device 500.

As mentioned above, image representations can be generated with the x-ray beam device 500 using an x-ray beam. The computer system 509 processes the data records that are based on the signals of the detector segments of the detector system 505, wherein, in the case of an appropriate selection of the detection segments and in the case of appropriate processing of the signals from the detection segments, it is possible, inter alia, to generate contrasts in the image representation which are caused by phase shifts in the x-ray radiation.

The features of the system described herein disclosed in the present description, in the drawings and in the claims can be essential for the realization of the system described herein in the various embodiments thereof, both individually and in arbitrary combinations. The system described herein is not restricted to the described embodiments. It can be varied within the scope of the claims, taking into account the knowledge of the relevant person skilled in the art.

What is claimed is:

1. A method for analyzing an object using a particle beam apparatus, the particle beam apparatus having at least one beam generator for generating a particle beam with charged particles, at least one objective lens for focusing the particle beam onto the object, wherein interaction particles are generated and/or interaction radiation is generated in the case of an interaction between the particle beam and the object, at least one vacuum region, in which at least one detector is arranged to detect the interaction particles and/or the interaction radiation, wherein the detector has at least one detection surface, wherein a multiplicity of detection units are arranged at the detection surface, wherein each detection unit of the multiplicity of detection units is individually actuatable and readable by way of a control device, at least one data memory, in which information is stored, wherein the information comprises information about an interaction behavior of the particle beam with the material of the object and/or information about solid angle regions, in which the interaction particles propagate after the generation thereof and/or into which the interaction radiation is emitted after the generation thereof, and at least one analysis unit for analyzing the object, the method comprising:

identifying at least one first group of detection units from the multiplicity of detection units using the information stored in the data memory;

forming a first detector segment from the first group of detection units;

loading information about the first detector segment into the control device;

guiding the particle beam onto the object and scanning the object using the particle beam;

detecting the interaction particles and/or interaction radiation with the detector, wherein a first detector segment signal is read from the first detector segment;

generating a representation of the object using the first detector segment signal; and analyzing the object using the representation of the object in the analysis unit.

2. The method as claimed in claim 1, further comprising:

loading information from the data memory into the control device, wherein identification of the first group of detection units is provided by the information loaded into the control device; and forming the first detector segment from the first group of detection units using the control device.

3. The method as claimed in claim 1, further comprising:

identifying at least a second group of detection units from the multiplicity of detection units;

forming a second detector segment from the second group of detection units;

loading information about the second detector segment into the control device; and reading a second detector segment signal from the second detector segment and generating the representation of the object using the second detector segment signal.

4. The method as claimed in claim 1, wherein the representation of the object is a first representation of the object the method further comprising: detecting the interaction particles and/or interaction radiation with the detector, wherein respectively one detection signal is read from each one of the detection units from the multiplicity of detection units using the control device; generating a second representation of the object using the read detection signals; and storing the second representation of the object in the data memory.

5. The method as claimed in claim 1, further comprising:

visually selecting the first group of detection units from the multiplicity of detection units; and storing the selected first group of detection units in the control device.

6. The method as claimed in claim 3, further comprising:
visually selecting the second group of detection units from the multiplicity of detection units; and
storing the selected second group of detection units in the control device.

7. The method as claimed in claim 1, wherein the information stored in the data memory includes an intensity distribution, the method further comprising:
identifying the first group of detection units from the multiplicity of detection units using the intensity distribution.

8. The method as claimed in claim 3, wherein the information stored in the data memory includes an intensity distribution, the method further comprising:
identifying the second group of detection units from the multiplicity of detection units using the intensity distribution.

9. The method as claimed in claim 3, further comprising:
reading and transmitting the first detector segment signal and the second detector segment signal to the analysis unit successively by way of a single line.

10. A computer program product comprising program code, which can be loaded into a processor and which, when executed, controls a particle beam apparatus having at least one beam generator for generating a particle beam with charged particles, at least one objective lens for focusing the particle beam onto the object, wherein interaction particles are generated and/or interaction radiation is generated in the case of an interaction between the particle beam and the object, at least one vacuum region, in which at least one detector is arranged to detect the interaction particles and/or the interaction radiation, wherein the detector has at least one detection surface, wherein a multiplicity of detection units are arranged at the detection surface, wherein each detection unit of the multiplicity of detection units is individually actuatable and readable by way of a control device, at least one data memory, in which information is stored, wherein the information comprises information about an interaction behavior of the particle beam with the material of the object and/or information about solid angle regions, in which the interaction particles propagate after the generation thereof and/or into which the interaction radiation is emitted after the generation thereof, and at least one analysis unit for analyzing the object, the computer program code, when executed by a processor, performing the following steps:
identifying at least one first group of detection units from the multiplicity of detection units using the information stored in the data memory;
forming a first detector segment from the first group of detection units;
loading information about the first detector segment into the control device;
guiding the particle beam onto the object and scanning the object using the particle beam;
detecting the interaction particles and/or interaction radiation with the detector, wherein a first detector segment signal is read from the first detector segment;
generating a representation of the object using the first detector segment signal; and
analyzing the object using the representation of the object in the analysis unit.

11. A particle beam apparatus for analyzing an object, comprising
a first particle beam generator for generating a first particle beam with first charged particles;
a first objective lens for focusing the first particle beam onto the object;
at least one vacuum region, in which at least one detector is arranged to detect interaction particles and/or interaction radiation, wherein the detector has at least one detection surface, wherein a multiplicity of detection units are arranged at the detection surface, wherein each detection unit of the multiplicity of detection units respectively generates a detection signal when it detects the interaction particles and/or the interaction radiation and wherein each detection unit of the multiplicity of detection units is individually actuatable and readable by way of a control device;
at least one data memory configured to store information during operation, wherein the information includes information about an interaction behavior of the first particle beam with the material of the object and/or information about solid angle regions, in which the interaction particles propagate after the generation thereof and/or into which the interaction radiation is emitted after the generation thereof;
at least one analysis unit for analyzing the object; and
at least one processor loaded with a computer program product containing code that, when executed by the processor, performs the following steps:
identifying at least one first group of detection units from the multiplicity of detection units using the information stored in the data memory;
forming a first detector segment from the first group of detection units;
loading information about the first detector segment into the control device;
guiding the particle beam onto the object and scanning the object using the particle beam;
detecting the interaction particles and/or interaction radiation with the detector, wherein a first detector segment signal is read from the first detector segment;
generating a representation of the object using the first detector segment signal; and
analyzing the object using the representation of the object in the analysis unit.

12. The particle beam apparatus as claimed in claim 11, wherein the control device is arranged in the vacuum region.

13. The particle beam apparatus as claimed in claim 11, wherein the detector includes a detector head, the detector head is arranged in the vacuum region, the detection surface is arranged on the detector head, and the control device is arranged in the detector head.

14. The particle beam apparatus as claimed in claim 11, further comprising:
a second beam generator for generating a second particle beam with second charged particles; and
a second objective lens for focusing the second particle beam onto the object.

15. The particle beam apparatus as claimed in claim 11, wherein the particle beam apparatus is an electron beam apparatus and/or an ion beam apparatus.

16. The method as claimed in claim 3, further comprising:
transmitting the first detector segment signal to the analysis unit by way of a first line and transmitting the second detector segment signal to the analysis unit by way of a second line.

* * * * *

UNITED STATES PATENT AND TRADEMARK OFFICE
CERTIFICATE OF CORRECTION

| | | |
|---|---|---|
| PATENT NO. | : 9,535,020 B2 | Page 1 of 1 |
| APPLICATION NO. | : 14/972589 | |
| DATED | : January 3, 2017 | |
| INVENTOR(S) | : Schillinger et al. | |

It is certified that error appears in the above-identified patent and that said Letters Patent is hereby corrected as shown below:

On the Title Page

Column 2 under FOREIGN PATENT DOCUMENTS, replace "DE 2009 024 928 A1" with -- DE 10 2009 024 928 A1 --.

In the Specification

Column 13, Line 67 to Column 14, Line 1, replace "10-1 Pa to 10-6 Pa" with -- 10-1 Pa to 10-5 Pa --.

Column 21, Line 21, replace "reBions" with -- regions --.

Signed and Sealed this
Tenth Day of October, 2017

Joseph Matal
*Performing the Functions and Duties of the*
*Under Secretary of Commerce for Intellectual Property and*
*Director of the United States Patent and Trademark Office*